United States Patent [19]

Artz

[11] Patent Number: 4,746,357
[45] Date of Patent: May 24, 1988

[54] HERBICIDAL ACETYLENIC TRIAZINES

[75] Inventor: Steven P. Artz, Kennett Square, Pa.

[73] Assignee: E. I. Du Pont de Nemours and Company, Wilmington, Del.

[21] Appl. No.: 52,610

[22] Filed: May 21, 1987

Related U.S. Application Data

[60] Division of Ser. No. 748,642, Jun. 27, 1985, Pat. No. 4,689,069, which is a continuation-in-part of Ser. No. 638,962, Aug. 8, 1984, abandoned.

[51] Int. Cl.$^4$ .............. C07D 251/16; C07D 401/12; C07D 417/12; A01N 43/68
[52] U.S. Cl. .......................... 71/93; 71/91; 71/90; 544/206; 544/207; 544/211; 544/212; 544/49
[58] Field of Search .............. 71/93, 90, 91; 544/206, 544/207, 211, 212, 49

[56] References Cited

U.S. PATENT DOCUMENTS

| 4,127,405 | 11/1978 | Levitt | 71/93 |
| 4,169,719 | 10/1979 | Levitt | 71/92 |
| 4,214,890 | 7/1980 | Levitt | 71/90 |
| 4,383,113 | 5/1983 | Levitt | 544/211 |
| 4,421,550 | 12/1983 | Selby et al. | 71/92 |
| 4,424,073 | 1/1984 | Levitt | 71/92 |

Primary Examiner—John M. Ford
Attorney, Agent, or Firm—James A. Costello

[57] ABSTRACT

Sulfonylureas derived from acetylenic pyrimidines and triazines, useful as pre- and postemergence herbicides. Typical of this group is 2-[[(4-ethynyl-6-methylpyrimidine-2-yl)aminocarbonyl]-aminosulfonyl]-benzoic acid, methyl ester.

39 Claims, No Drawings

HERBICIDAL ACETYLENIC TRIAZINES

CROSS-REFERENCE TO RELATED APPLICATIONS

This application is a division of application bearing U.S. Ser. No. 748,642, filed June 27, 1985, now U.S. Pat. No. 4,689,069 which is a continuation-in-part of application bearing U.S. Ser. No. 638,962, filed on Aug. 8, 1984, now abandoned.

BACKGROUND OF THE INVENTION

U.S. Pat. No. 4,127,405 and U.S. Pat. No. 4,169,719 disclose herbicidal benzenesulfonylureas.

EP-A-9,419 discloses herbicidal sulfonamides of formula

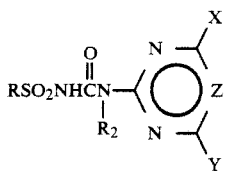

where
R is

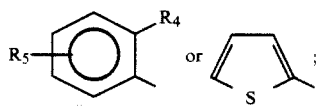

$R_4$ is Cl, Br, F, $NO_2$, $CH_3$, $OCH_3$, $CF_3$ or $S(O)_nR_3$;
$R_5$ is $C_1$-$C_6$ alkyl or $C_3$-$C_4$ alkenyl;
n is 0, 1 or 2;
X is $CH_3$ or $OCH_3$;
Z is CH or N; and
Y is, among other values, $C_2$-$C_4$ alkynyl;

U.S. Pat. No. 4,383,113 discloses herbicidal benzenesulfonamides of formula

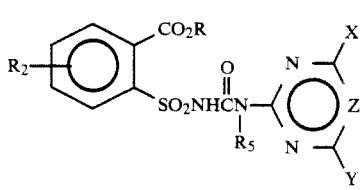

where
R can be, among other values, $C_1$-$C_{12}$ alkyl, $C_3$-$C_{10}$ alkenyl or $C_2$-$C_6$ alkyl substituted with one to four substituents selected from 0–3 atoms of F, Cl or Br, 0–2 methoxy groups and 0–1 cyano groups;
X is H, Cl, $CH_3$, $OCH_3$, $OCH_2CH_3$ or $OCH_2CH_2OCH_3$; and
Y is, among other values, $CH_2C\equiv CR_{13}$ where $R_{13}$ is H, $CH_3$ or $CH_2Cl$.

U.S. Pat. No. 4,421,550 discloses herbicidal sulfonamides of formula

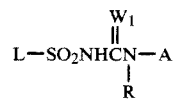

where
$R_1$ can be, among other values, $C_3$-$C_4$ alkynyl;
$R_2$ can be, among other values, $C_1$-$C_4$ alkyl or $C_1$-$C_4$ alkyl substituted with 1–3 F atoms; and
Z can be, among other values, optionally substituted phenyl, benzyl, 1-naphthyl, 3-pyridyl or 2- or 3-thienyl.

SUMMARY OF THE INVENTION

This invention relates to compounds of Formula I, agriculturally suitable compositions containing them, and use of these compounds and compositions as pre-emergent and/or postemergent herbicides or plant growth regulants.

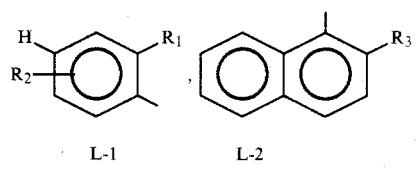

wherein
$W_1$ is O or S;
R is H or $CH_3$;
L is

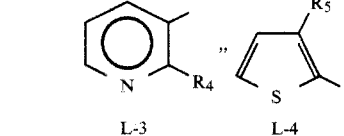

L-1    L-2

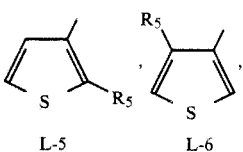

L-3    L-4

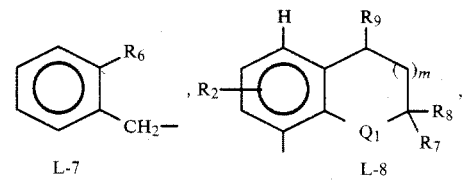

L-5    L-6

L-7    L-8

-continued

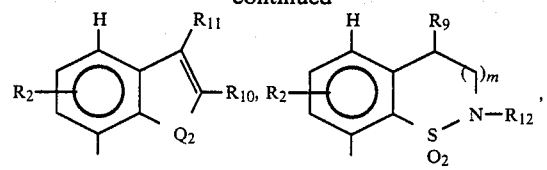

L-9  L-10

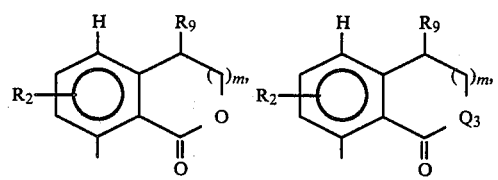

L-11  L-12

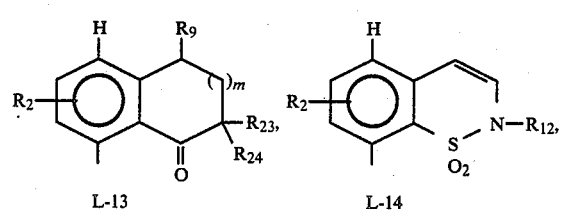

L-13  L-14

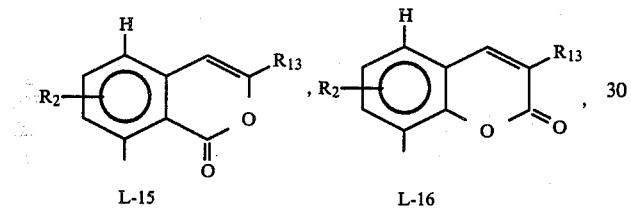

L-15  L-16

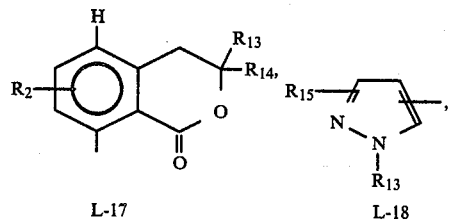

L-17  L-18

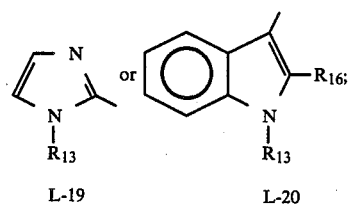

L-19  L-20

$R_1$ is $OCH_2CH_2OCH_3$, $CO_2R_{17}$, $SO_2NR_{18}R_{19}$, $SO_2N(OCH_3)CH_3$, $OSO_2R_{20}$, $WCF_3$, $WCHF_2$, $C_3$-$C_4$ alkenyloxy, $C_3$-$C_4$ alkynyloxy, $C_1$-$C_2$ alkyl substituted with $OCH_3$ or $OCH_2CH_3$, $C_6H_5$, $C_3$-$C_4$ alkynyl, $CH{=}CHCF_3$, $CH{=}CHBr$, or Q;

Q is

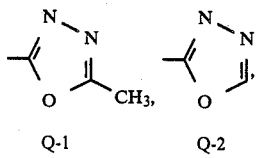

Q-1  Q-2

-continued

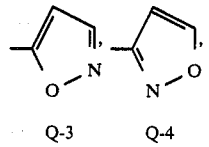

Q-3  Q-4

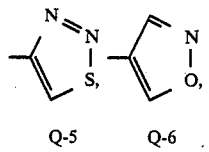

Q-5  Q-6

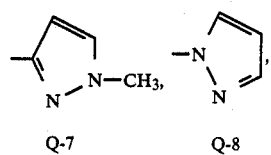

Q-7  Q-8

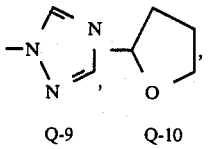

Q-9  Q-10

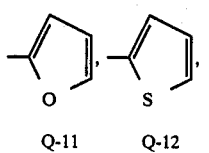

Q-11  Q-12

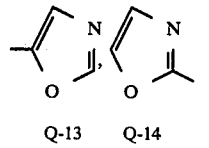

Q-13  Q-14

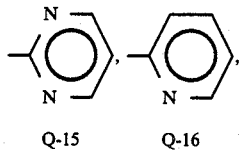

Q-15  Q-16

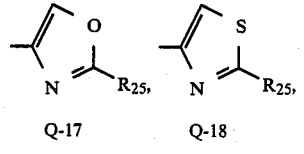

Q-17  Q-18

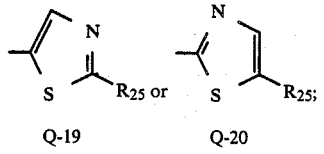

Q-19  Q-20

$R_2$ is H, F, Cl, Br, $CF_3$, $C_1$-$C_2$ alkyl, $C_1$-$C_2$ alkoxy, $C_1$-$C_2$ alkylthio, $C_2$-$C_3$ alkoxyalkyl, $C_2$-$C_3$ alkylthioalkyl or $OCF_2H$;

$R_3$ is H, $CH_3$, $OCH_3$, F, Cl, Br, $SO_2N(CH_3)_2$, $OSO_2CH_3$ or $S(O)_nCH_3$;

$R_4$ is $CH_3$, $CH_2CH_3$, $OCH_3$, $OCH_2CH_3$, F, Cl, Br, $SO_2NR_{18}R_{19}$, $SO_2N(OCH_3)CH_3$, $S(O)_nR_{21}$, $C_3-C_4$ alkenyloxy, $CH_2OCH_3$ or $CH_2OCH_2CH_3$;

$R_5$ is $C_1-C_3$ alkyl, F, Cl, Br, $NO_2$, $CO_2R_{17}$, $SO_2NR_{18}R_{19}$, $SO_2N(OCH_3)CH_3$ or $S(O)_nR_{21}$;

$R_6$ is Cl, $NO_2$, $CO_2CH_3$, $CO_2CH_2CH_3$, $SO_2N(CH_3)_2$, $OSO_2CH_3$, $SO_2CH_3$, $SO_2CH_2CH_3$, $OCH_3$ or $OCH_2CH_3$;

$R_7$ is H, $CH_3$ or $CH_2CH_3$;

$R_8$ is H, $CH_3$ or $CH_2CH_3$;

$R_9$ is H or $CH_3$;

$R_{10}$ is H or $CH_3$;

$R_{11}$ is H or $CH_3$;

$R_{12}$ is H, $C_1-C_5$ alkyl, $C_2-C_3$ alkoxycarbonyl, $C_2-C_3$ alkylcarbonyl, $C_1-C_3$ alkyl substituted by 1-3 halogens selected from 0-3 F, 0-3 Cl or 0-1 Br, $C_2-C_4$ alkyl substituted by $OCH_3$, $C_3-C_4$ alkenyl, $C_3-C_4$ alkynyl or benzyl;

$R_{13}$ is H or $C_1-C_3$ alkyl;

$R_{14}$ is H or $CH_3$;

$R_{15}$ is $C_1-C_3$ alkyl, F, Cl, Br, $NO_2$, $CO_2R_{17}$, $SO_2NR_{18}R_{19}$, $SO_2R_{21}$ or $OCF_2H$;

$R_{16}$ is H, $CO_2CH_3$, $CO_2CH_2CH_3$, $SO_2CH_3$ or $SO_2CH_2CH_3$;

$R_{17}$ is $C_1-C_4$ alkyl, $CH_2CH_2OCH_3$, $CH_2CH_2Cl$ or $CH_2CH=CH_2$;

$R_{18}$ is H or $C_1-C_3$ alkyl;

$R_{19}$ is $C_1-C_3$ alkyl;

$R_{20}$ is $C_1-C_3$ alkyl or $N(CH_3)_2$;

$R_{21}$ is $C_1-C_3$ alkyl or $CH_2CH=CH_2$;

$R_{22}$ is H or $C_1-C_3$ alkyl;

$R_{23}$ is H or Cl;

$R_{24}$ is H or Cl;

$R_{25}$ is H or $CH_3$;

m is 0 or 1;

n is 0 or 2;

$Q_1$ is O, S, $SO_2$ or $NR_{14}$;

$Q_2$ is O or S;

$Q_3$ is S or $NR_{22}$;

W is O, S or $SO_2$;

A is

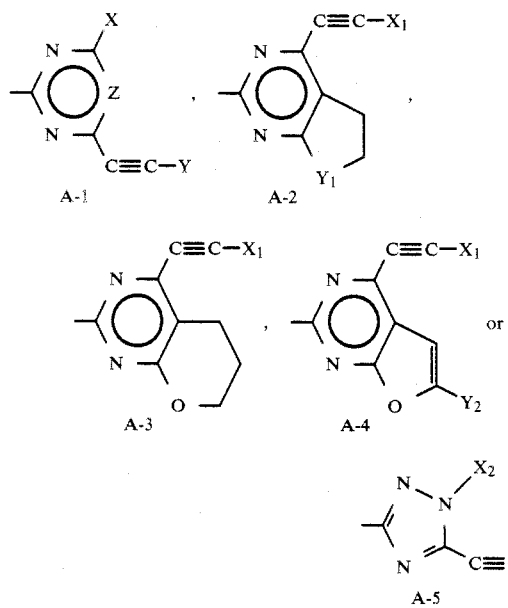

X is H, $C_1-C_3$ alkyl, $C_1-C_3$ alkoxy, $C_1-C_3$ haloalkyl, $C_1-C_3$ haloalkoxy, $C_2-C_4$ alkoxyalkoxy, $C_1-C_3$ alkylamino, di($C_1-C_2$ alkyl)amino, amino or cyclopropyl;

Y is H, $C_1-C_5$ alkyl, Br, I, phenyl optionally substituted with $CH_3$, $OCH_3$, halogen, $NO_2$, $CF_3$ or $SCH_3$, or $C_1-C_3$ alkyl substituted with OH, $OCH_3$, $OC_2H_5$ or F;

Z is CH or N;

$X_1$ is H or $CH_3$;

$Y_1$ is O or $CH_2$;

$X_2$ is $CH_3$, $CH_2CH_3$ or $CH_2CF_3$; and $Y_2$ is H or $CH_3$;

and their agriculturally suitable salts; provided that (1) the total number of carbon atoms of $R_{18}$ and $R_{19}$ is less than or equal to four;

(2) when m is 1, then $R_9$ is H;

(3) when L is L-17, then $R_{13}$ and $R_{14}$ are not simultaneously H;

(4) when L is L-18, then $R_{15}$ is adjacent to the sulfonylurea bridge $SO_2NHC(W_1)N(R)A$;

(5) when L is L-8 and $Q_1$ is $NR_{14}$, then m is 1;

(6) when A is A-5 and L is L-1, L-2, L-3, L-4, L-5, L-6 or L-7, then $X_1$ is H;

(7) when the total number of carbon atoms of X and Y is greater than four, then the combined number of carbons of the substituents on L is less than or equal to four; and (8) when L is L-8, L-9, L-11, L-12 or L-17 and $R_2$ is $C_2-C_3$ alkoxyalkyl or $C_2-C_3$ alkylthioalkyl, then Y is other than H or $C_1-C_2$ alkyl.

In the above definitions, the term "alkyl" used either alone or in compound words such as "alkylthio" or "haloalkyl", denotes straight chain or branched alkyl, e.g., methyl, ethyl, n-propyl, isopropyl and the different butyl or pentyl isomers.

Alkoxy denotes methoxy, ethoxy, n-propoxy and isopropoxy.

Alkenyl denotes straight chain or branched alkenes, e.g., 1-propenyl, 2-propenyl, 3-propenyl and the different butenyl isomers.

Alkynyl denotes straight chain or branched alkynes, e.g., ethynyl, 1-propynyl, 2-propynyl and the different butynyl isomers.

Alkylcarbonyl denotes acetyl or propionyl, and the term alkylamino is defined in an analogous manner.

The term "halogen", either alone or in compound words such as "haloalkyl", denotes fluorine, chlorine, bromine or iodine.

In terms such as $C_2-C_3$ alkylthioalkyl, the specified number of carbon atoms is meant to define the total number of carbon atoms in that substituent group. For example, $C_2-C_3$ alkylthioalkyl would designate $CH_2SCH_3$, $CH_2SC_2H_5$, $CH_2CH_2SCH_3$ or $CH(CH_3)SCH_3$.

Preferred for reasons of their higher herbicidal activity and/or more favorable ease of synthesis are:

(1) Compounds of Formula I where R is H, $W_1$ is O and A is A-1, A-2, A-3 or A-4;

(2) Compounds of Preferred Group 1 where Y is H or $C_1-C_3$ alkyl;

(3) Compounds of Preferred Group 2 where L is L-1, L-2, L-3, L-4, L-5, L-6, L-8, L-9, L-10, L-11, L-12, L-13, L-17 or L-18, $Q_1$ is O, S or $SO_2$ and X is $CH_3$, $CH_2CH_3$, $OCH_3$, $OCH_2CH_3$, $CH_2OCH_3$, $CH_2OCH_2CH_3$, $OCH_2CF_3$, $OCH_2CF_2H$, $OCH_2CH_2F$ or $OCF_2H$;

(4) Compounds of Preferred Group 3 where $R_1$ is $CO_2R_{17}$, $SO_2NR_{18}R_{19}$, $SO_2N(OCH_3)CH_3$, $WCF_3$, $WCHF_2$,

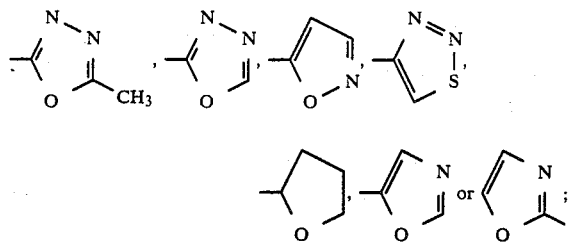

$R_2$ is H, F, Cl, $CH_3$, $OCH_3$ or $SCH_3$;
$R_3$ is $CH_3$, $OCH_3$, Cl, Br, $OSO_2CH_3$ or $S(O)_nCH_3$;
$R_4$ is $CH_3$, $OCH_3$, Cl, $SO_2N(CH_3)_2$, $SO_2CH_3$ or $SO_2CH_2CH_3$;
$R_5$ is $CH_3$, Cl, $NO_2$, $CO_2R_{17}$, $SO_2N(CH_3)_2$, $SO_2CH_3$ or $SO_2CH_2CH_3$;
$R_7$ is H or $CH_3$;
$R_8$ is H or $CH_3$;
$R_9$ is H;
$R_{11}$ is H;
$R_{12}$ is H, $C_1$-$C_4$ alkyl, $CH_2CH_2OCH_3$ or $CH_2CH=CH_2$;
$R_{13}$ is H or $CH_3$;
$R_{15}$ is $CH_3$, $CH_2CH_3$, Cl, $NO_2$, $CO_2CH_3$, $CO_2CH_2CH_3$, Br, $SO_2N(CH_3)_2$, $SO_2CH_3$, $SO_2CH_2CH_3$ or $OCF_2H$;
$R_{18}$ is H or $CH_3$;
$R_{19}$ is $C_1$-$C_2$ alkyl; and
W is O or S;

(5) Compounds of Preferred Group 4 where A is A-1, X is $CH_3$, $CH_2CH_3$, $OCH_3$ or $OCH_2CH_3$ and Y is H or $CH_3$;
(6) Compounds of Preferred Group 5 where L is L-1 and $R_1$ is $CO_2CH_3$, $CO_2CH_2CH_3$, $SO_2N(CH_3)_2$, or $OCF_2H$;
(7) Compounds of Preferred Group 5 where L is L-2;
(8) Compounds of Preferred Group 5 where L is L-4;
(9) Compounds of Preferred Group 5 where L is L-5;
p1 (10) Compounds of Preferred Group 5 where L is L-8;
(11) Compounds of Preferred Group 5 where L is L-9;
(12) Compounds of Preferred Group 5 where L is L-10;
(13) Compounds of Preferred Group 5 where L is L-11;
(14) Compounds of Preferred Group 5 where L is L-12;
(15) Compounds of Preferred Group 5 where L is L-13;
(16) Compounds of Preferred Group 5 where L is L-17; and
(17) Compounds of Preferred Group 5 where L is L-18.

Especially preferred for reason of highest herbicidal efficacy and/or greatest ease of synthesis are:
(i) 2-[[(4-ethynyl-6-methylpyrimidin-2-yl)aminocarbonyl]aminosulfonyl]benzoic acid, methyl ester, m.p. 185° to 190° C.;
(ii) 2-[[(4-ethynyl-6-methoxy-1,3,5-triazin-2-yl)aminocarbonyl]aminosulfonyl]benzoic acid, methyl ester, m.p. 158° to 161° C.(d); and
(iii) N'-[(4-ethynyl-6-methoxy-1,3,5-triazin-2-yl)aminocarbonyl]-N,N-dimethyl-1,2-benzenedisulfonamide, m.p. 135° to 139° C.(d).

DETAILS OF THE INVENTION

Synthesis

The compounds of Formula I can be prepared by one or more of the methods described below in Equations 1, 2, 3, and 4.

As shown in Equation 1, compounds of Formula I where L is other than L-20 can be prepared by reacting a sulfonyl isocyanate of Formula II with an appropriate heterocyclic amine of Formula III.

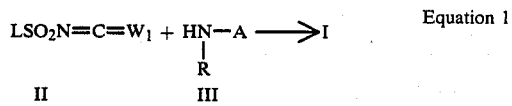

Equation 1

The reaction is carried out at 25° to 100° C. in an inert, aprotic solvent such as methylene chloride or xylene for 0.5 to 24 hours as taught in U.S. Pat. No. 4,127,405.

Compounds of Formula I, where $R_1$, $R_5$ and $R_6$ of the structures designated L are other than $CO_2R_{17}$, and L is not $L_{11}$, $L_{12}$, $L_{15}$ or $L_{17}$, can be prepared by reacting the sulfonamides of Formula IV with an appropriate methyl carbamate of Formula V in the presence of at least an equimolar amount of trimethylaluminum, as shown in Equation 2.

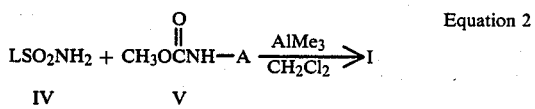

Equation 2

The reaction is carried out at 25° to 40° C. in a solvent such as methylene chloride for 10 to 96 hours under an inert atmosphere as taught in EPO No. 84,244 (published July 27, 1983). The required carbamates V are prepared by reacting the corresponding amines III with dimethylcarbonate or methyl chloroformate in the presence of a strong base.

Alternatively, compounds of Formula I can be prepared by reacting a sulfonylcarbamate of Formula VI with an appropriate amine of Formula III, as shown in Equation 3.

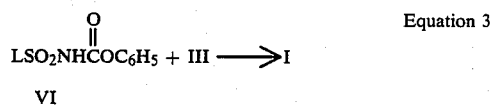

Equation 3

The reaction is carried out at 50° to 100° C. in a solvent such as dioxane for 0.5 to 24 hours as taught in EPO publication No. 44807. The required carbamates VI are prepared by reacting the corresponding sulfonamides IV with diphenylcarbonate in the presence of a strong base.

Additionally, compounds of Formula I can be prepared by reacting a sulfonamide of Formula IV with an appropriate heterocyclic phenyl carbamate of Formula VII in the presence of a nonnucleophilic base such as 1,8-diazabicyclo[5.4.0]undec-7-ene (DBU) as shown below in Equation 4.

Equation 4

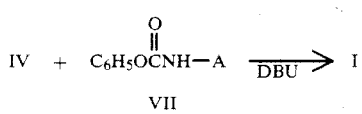

The reaction is carried out at 20° to 100° C. in an inert solvent, such as dioxane, for 0.5 to 24 hours by the methods taught in EPO publication No. 44807. The required carbamates, VII, are prepared by reacting the corresponding heterocyclic amines, III, with phenylchloroformate in the presence of a base.

The intermediate sulfonyl isocyanates of Formula II in Equation 1 can be prepared as shown in Equations 5 and 6.

As shown in Equation 5, sulfonyl isocyanates of Formula II can be prepared by the reaction of sulfonamides of Formula IV with phosgene in the presence of n-butyl isocyanate and a tertiary amine catalyst, such as 1,4-diazabicyclo[2.2.2]octane (DABCO), at reflux in a solvent such as xylene by the method of U.S. Pat. No. 4,238,621.

Equation 5

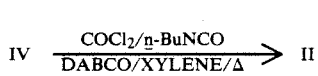

The sulfonyl isocyanates can also be prepared from the sulfonamides by a two step procedure involving (a) reacting the sulfonamides with n-butyl isocyanate in the presence of a base such as $K_2CO_3$ at reflux in an inert solvent such as 2-butanone forming a n-butyl sulfonylurea; and (b) reacting this compound with phosgene and a tertiary amine catalyst at reflux in xylene solvent. The method is similar to a procedure taught by Ulrich and Sayigh, *Newer Methods of Preparative Organic Chemistry*, Vol. VI, p. 223-241, Academic Press, New York and London, W. Forest Ed.

Alternatively, as shown in Equation 6, the sulfonyl isocyanates of Formula II can be prepared by reacting the corresponding sulfonyl chlorides VIII with cyanic acid salts.

Equation 6

The reaction is carried out at 25° to 100° C. in an inert aprotic solvent such as acetonitrile for 0.5-24 hours in the presence of phosphorous pentoxide and an alkali metal salt such as lithium iodide, according to the teachings of Japanese Pat. No. 76/26,816 (*Chem. Abst.*, 85:77892e (1976)).

Sulfonyl isothiocyanates of Formula II, where $W_1$ is S, can be prepared according to the methods taught by K. Hartke, *Arch. Pharm.*, 299, 174 (1966).

As shown in Equation 7, sulfonamides of Formula IV can be prepared from the corresponding sulfonyl chlorides of Formula VIII by contacting with either anhydrous or aqueous ammonia.

Equation 7

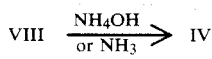

The preparation of sulfonamides from sulfonyl chlorides is widely reported in the literature, for reviews see: Hawking et al., "The Sulfonamides," H. K. Lewis and Co., London, 1950 and Northey, "The Sulfonamides and Allied Compounds," Reinhold Publishing Corp., New York, 1948.

The requisite sulfonyl chlorides of Formula VIII can be synthesized by known methods or with slight modifications thereof, by one skilled in the art. Several representative teachings are listed below. Sulfonyl chlorides, where L is L-1 are described generally in U.S. Pat. No. 4,127,405 and more specifically for o-esters in U.S. Pat. No. 4,394,506; o-sulfonamides in U.S. Pat. No. 4,310,346; o-fluoro-substituted-methyls and -methoxys in EP-A-23,422; o-heterocycles in EP-A-83,975 and EP-A-85,476; and o-sulfonates in U.S. Pat. No. 4,435,205. Additionally, sulfonyl chlorides of Formula VIII can be made according to the teachings in U.S. Pat. No. 4,370,479, EP-A-13,480, EP-A-64,804, EP-A-30,142 and U.S. Pat. No. 4,398,939, U.S. Pat. No. 4,420,325, EP-A-107,979 and EP-A-95,925 for $L_2$, $L_3$, $L_4$ to $L_6$, $L_7$, $L_8$ to $L_{17}$ and $L_{18}$ to $L_{19}$.

Heterocycles of Formula III can be synthesized by the route shown in Equation 8a and 8b; where J is Cl, Br or I; L' is a neutral ligand such as triphenyl phosphine; P is $C(CH_3)_2OH$ or $SiMe_3$; T is U where J is $-C\equiv C-P$ and
U is

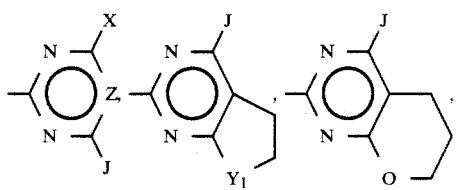

U-1    U-2    U-3

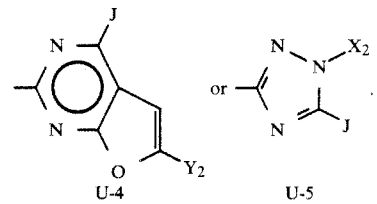

U-4    U-5

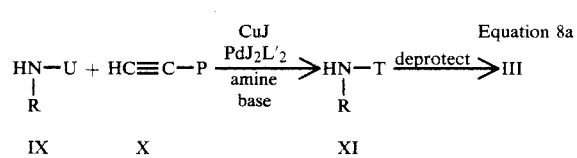

Equation 8a

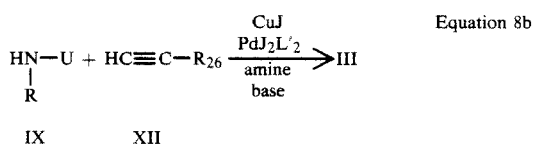

Equation 8b wherein $R_{26}$ is Y, but not H, Br or I.

The reaction is carried out at 20° to 100° C. for 0.5 to 48 hours by mixing the haloheterocycle of Formula IX with a terminal acetylene of Formula X or XII (one or more equivalents), copper (I) halide (0.005 to 0.1 equivalents), palladium catalyst (0.005 to 0.1 equivalents), an alkylamine solvent such as diethylamine or an inert solvent such as dichloromethane or tetrahydrofuran (THF) plus a tertiary amine (2 to 100 equivalents) such as triethylamine. However, when Z is N only the second solvent system is used. The palladium coupling of terminal acetylenes to aromatic halides is well known in the literature. Methods similar to the above reactions are taught by K. Edo, T. Sakamoto and H. Yamanaka in *Chem. Pharm. Bull.*, 26 (1978), 3843–3850.

P is a protecting group which can be removed by methods known in the literature. When P is a 2-hyroxy-2-propyl moiety, removal of it to the ethyne is effected with an alkali hydroxide in an inert solvent such as toluene at 20° to 130° C. for 0.5 to 24 hours. A similar procedure is taught by D. Ames, D. Bull and C. Takundwa in *Synthesis*, 1981, 364–365.

When P is a trimethylsilyl moiety, it can be removed by mixing the trimethylsilyl protected acetylene in methanol with dilute alkali hydroxide at 0° to 80° C. for 0.5 to 25 hours. The method is similar to that taught by S. Takahasi, Y. Kuroyama, K. Sonogashira and N. Hagihara in *Synthesis*, 1980, 627–630.

The requisite haloheterocycles of Formula IX where R is H or $CH_3$ are either known or can be prepared by methods known to one skilled in the art.

Additionally, alkynyl triazines may be prepared by the route shown in Equation 9. A procedure is described in U.S. Pat. No. 3,778,441.

Equation 9

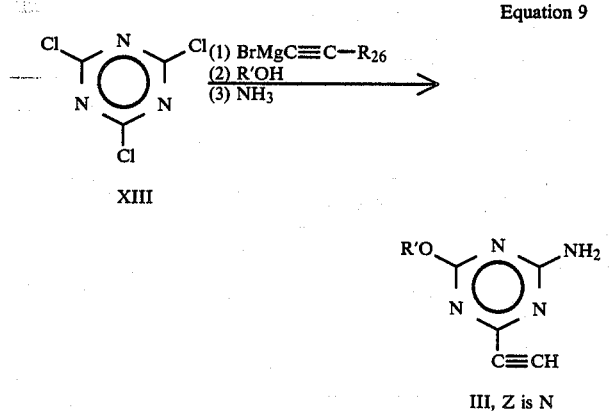

where R' is $C_1$ to $C_3$ alkyl or $CH_2CH_2OCH_3$.

Derivatization of terminal acetylenes is well known in the literature. Several general transformations are shown below in Equation 10.

Equation 10

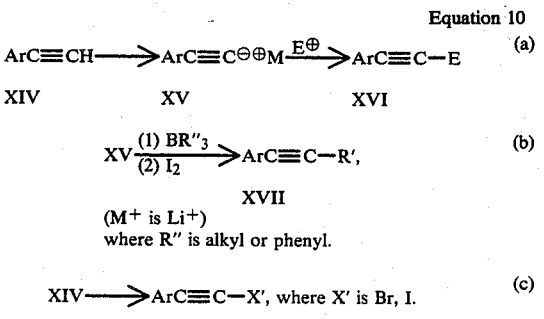

Literature examples may be found in Yamaguchi, et. al., *Tet. Let.*, 24 (1983), 391 to 394; Suzuki, et. al., *J. Am. Chem. Soc.*, 95, 3080 (1973); and Hofmeister, et. al., *Angew Chem. Int. Ed. Engl.*, 23 (1984), 727 to 729; for Equations 10a, b, and c, respectively.

For a review of the synthesis and reactions of 2-aminopyrimidines (III, U is U-1 and Z=CH) see *The Chemistry of Heterocyclic Compounds*, Vol. 16, John Wiley and Sons, New York (1962). For a review of the synthesis and reactions of 2-amino-s-triazines (III, U is U-1 and Z=N) see *The Chemistry of Heterocyclic Compounds*, Vol. 13, John Wiley, New York (1959), F. C. Schaefer, U.S. Pat. No. 3,154,547 and F. C. Schaefer and K. R. Huffman, *J. Org. Chem.*, 28, 1812 (1963). Also, a method for the synthesis of 2-ethynyl-4-amino-6-methoxy-s-triazine is taught in U.S. Pat. No. 3,778,441.

The synthesis of bicyclic amines where U is U-2 or U-3 is taught in U.S. Pat. No. 4,339,267. The synthesis of bicyclic amines where U is U-4 is taught in EP-A-46,677. The synthesis of triazoles where U is U-5 is taught in U.S. Pat. No. 4,421,550.

Additionally, heterocylic amines where A is A-1 and Z is N are either known or can be prepared by methods taught in Ger. Offen. No. 2,209,470.

Heterocycles of Formula III where R is $CH_3$ may be prepared by the reaction sequence shown in Equation 8. When Z is N, these compounds may often be more conveniently synthesized by reaction of the corresponding compound of formula A—Cl with methylamine by procedures similar to those disclosed in Ger. Offen. No. 2,209,470 for analogous reactions with ammonia.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium, or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is illustrated by the following Examples, wherein temperatures are given in degrees Centigrade.

EXAMPLE 1

4-(2-Amino-4-methylpyrimidin-4-yl)-3-butyne-2-ol

A mixture of 10.0 g of 2-amino-4-chloro-6-methylpyrimidine, 8.8 ml of 2-methyl-3-butyn-2-ol, 400 ml of tetrahydrofuran (THF), 0.06 g of copper (I) iodide, 0.5 g of bis(triphenylphosphine)palladium (II) chloride and 20.4 ml of triethylamine was heated overnight at reflux under a nitrogen atmosphere. The reaction mixture was allowed to cool. It was then partitioned between 200 ml of ethyl acetate and 100 ml of sodium bicarbonate. The organic layer was washed successively with 100 ml of water and 100 ml of brine. The organic layer was dried (MgSO$_4$), filtered and concentrated under reduced pressure. The residue was placed on a silica gel dry column and eluted with dichloromethane/ethyl acetate/THF (10:90:0.1). The product band was extracted with THF. The organic extract was concentrated. Trituration of the residue (butyl chloride) gave 4.44 g of the title compound as a solid, m.p. 155°; PMR (90 MHz, CDCl$_3$) δ1.65(s, 6H, CH$_3$), 2.3(s, CH$_3$, 3H), 2.8(s, OH, 1H), 5.2(bs, 2H, NH$_2$), 6.6(s, Het-H, 1H); IR(nujol) 2221(w, C≡C) cm$^{-1}$.

EXAMPLE 2

2-Amino-4-ethynyl-6-methylpyrimidine

A mixture of 4.44 g of 4-(2-amino-4-methylpyrimidin-4-yl)-3-butyne-2-ol, 1 g of sodium hydroxide, 5 ml of dioxan and 50 ml of toluene was refluxed for two hours. The toluene layer was decanted from the residue, concentrated under reduced pressure and chromatographed on a silica gel dry column. The product band eluted with (2:3:0.5) ethyl acetate/dichloromethane/THF. Extraction with THF and concentration of the solvent gave 0.75 g of the title compound as a solid, 129°–130° dec.; IR(nujol) 2119 (w, C≡C) cm$^{-1}$; PMR(60 MHz, CDCl$_3$) δ2, 3(s, CH$_3$, 3H), 3.1(s, C≡CH, 1H), 5.3–5.6(bs, NH$_2$, 2H), 6.6(s, Het-H, 1H).

EXAMPLE 3

2-[[(4-Ethynyl-6-methylpyrimidin-3-yl)aminocarbonyl]aminosulfonyl]benzoic acid, methyl ester In a dry flask under a nitrogen atmosphere was mixed 0.24 g of 2-amino-4-ethenyl-6-methylpyrimidine, 0.61 g of 2-carbomethoxybenzenesulfonylisocyanate and 25 ml of dry dichloromethane. The solution was heated to reflux for five minutes and allowed to stir at room temperature overnight. A precipitate formed. The reaction mixture was stripped, triturated with butyl chloride to give 0.56 g of the title compound as a solid, m.p. 185°–190° (dec); IR(nujol) 2111 (C≡C), 3250 (NH), 3321 (NH), 1716 (CO) and 1725 (CO) cm$^{-1}$.

The invention is further exemplified by the compounds of Tables I to XX which can be prepared as described in Equations 1–10 and Examples 1–3 or by modifications thereof known to those skilled in the art.

---

KEY OF GENERAL STRUCTURES

The following structures are designated as shown in Tables I–XX.

General Structure I
wherein W$_1$ is O
unless otherwise indicated.

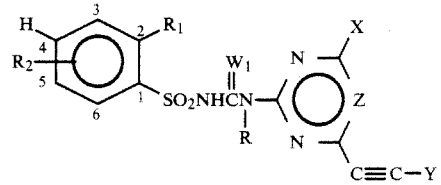

General Structure II

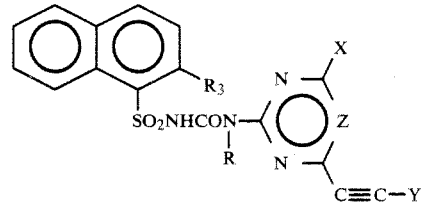

General Structure III

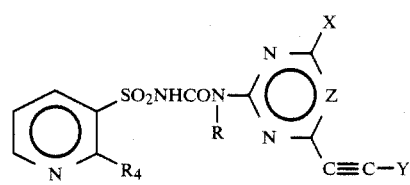

General Structure IV, IVA and IVB

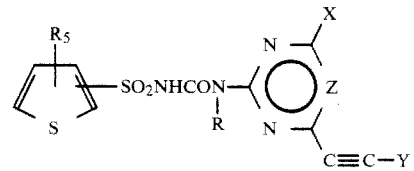

KEY OF GENERAL STRUCTURES
The following structures are designated as shown in Tables I-XX.
General Structure V
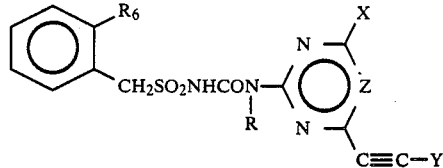
General Structure VI
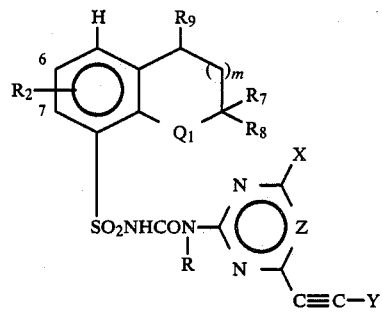
General Structure VII
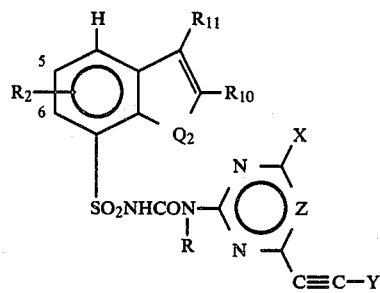
General Structure VIII
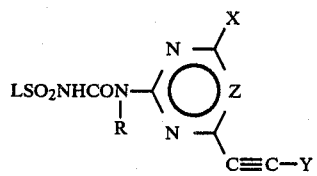
General Structure IX
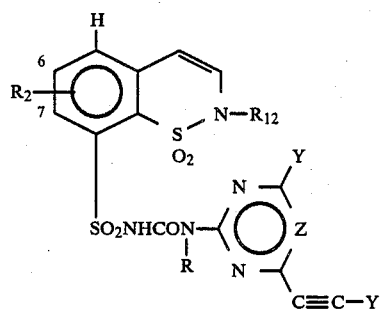
General Structure X
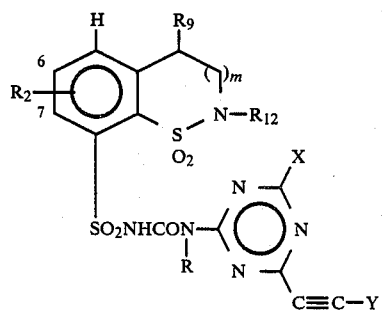

-continued
KEY OF GENERAL STRUCTURES
The following structures are designated as shown in Tables I-XX.
General Structure XI
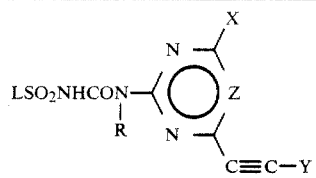
General Structure XII
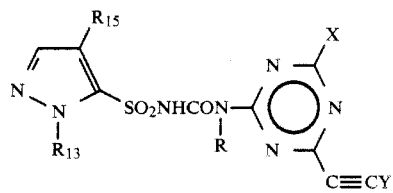
General Structure XIIA
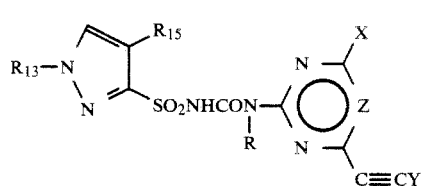
General Structure XIIB
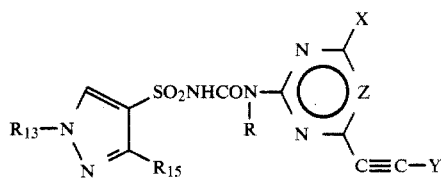
General Structure XIII
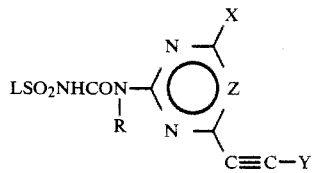
General Structure XIV
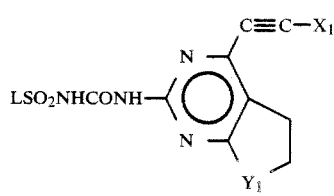
General Structure XV
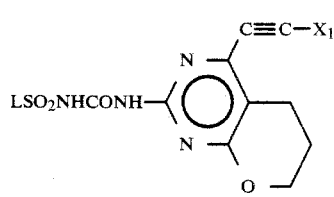
General Structure XVI
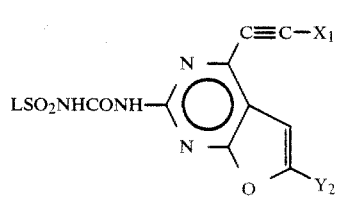

KEY OF GENERAL STRUCTURES
The following structures are designated as shown in Tables I–XX.

General Structure XVII

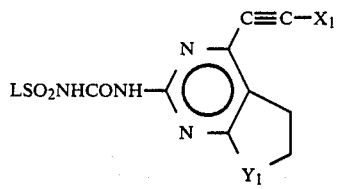

General Structure XVIII

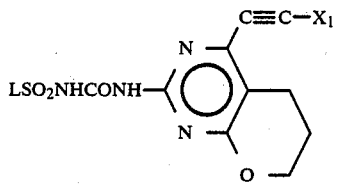

General Structure XIX

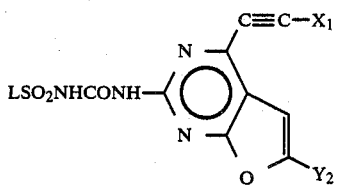

General Structure XX

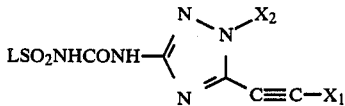

TABLE I
General Structure I

| $R_1$ | $R_2$ | R | X | Y | Z | m.p. °C. |
|---|---|---|---|---|---|---|
| $OCH_2CH_2OCH_3$ | H | H | $CH_3$ | H | CH | |
| $CO_2CH_3$ | H | H | $CH_3$ | H | CH | 185–190° |
| $CO_2CH_3$ | H | H | $OCH_3$ | H | CH | 173–180° |
| $CO_2CH_3$ | H | H | $OCH_3$ | H | N | 158–161°(d) |
| $CO_2CH_3$ | H | $CH_3$ | $OCH_3$ | $CH_3$ | N | |
| $CO_2CH_3$ | H | H | $OCH_3$ | $C_2H_5$ | CH | |
| $CO_2CH_3$ | H | H | $OCH_3$ | $(CH_2)_2CH_3$ | N | |
| $CO_2C_2H_5$ | H | H | $CH_3$ | H | N | |
| $CO_2C_2H_5$ | H | H | $OCH_3$ | H | CH | |
| $CO_2C_2H_5$ | H | H | $OCH_3$ | H | N | |
| $CO_2CH(CH_3)_2$ | H | H | $CH_3$ | H | CH | |
| $CO_2(CH_2)_3CH_3$ | H | H | $OCH_3$ | H | N | |
| $CO_2CH_2CH=CH_2$ | H | H | $OCH_3$ | H | CH | |
| $CO_2CH_2CH_2Cl$ | H | H | $OCH_3$ | H | CH | |
| $CO_2CH_2CH_2OCH_3$ | H | H | $OCH_3$ | H | CH | |
| $CO_2CH_3$ | H | H | $C_2H_5$ | H | CH | |
| $CO_2CH_3$ | H | H | $OC_2H_5$ | H | CH | |
| $CO_2CH_3$ | H | H | $OC_2H_5$ | H | N | 150–153° |
| $CO_2CH_3$ | H | H | $CH_2OCH_3$ | H | CH | |
| $CO_2CH_3$ | H | H | $CH_2OC_2H_5$ | H | CH | |
| $CO_2CH_3$ | H | H | $OCH_2CF_3$ | H | CH | |
| $CO_2CH_3$ | H | H | $OCH_2CF_2H$ | H | CH | |
| $CO_2CH_3$ | H | H | $OCH_2CH_2F$ | H | CH | |
| $CO_2CH_3$ | H | H | $OCF_2H$ | H | CH | |
| $CO_2CH_3$ | 5-Cl | H | $CH_3$ | H | CH | |
| $CO_2CH_3$ | 5-$OCH_3$ | H | $OCH_3$ | H | N | |
| $CO_2CH_3$ | 5-$CH_3$ | H | $OCH_3$ | H | CH | |
| $CO_2CH_3$ | 3-F | H | $CH_3$ | H | CH | |
| $CO_2CH_3$ | 5-Br | H | $OCH_3$ | H | N | |
| $CO_2CH_3$ | 5-$OCF_2H$ | H | $OCH_3$ | H | CH | |
| $SO_2N(CH_3)_2$ | H | H | $CH_3$ | H | CH | |
| $SO_2N(CH_3)_2$ | H | H | $OCH_3$ | H | CH | |
| $SO_2N(CH_3)_2$ | H | H | $OCH_3$ | H | N | 135–139°(d) |
| $SO_2N(CH_3)_2$ | H | H | $OC_2H_5$ | H | N | 150–153° |
| $SO_2N(CH_3)C_2H_5$ | H | H | $OCH_3$ | H | CH | |
| $SO_2N(C_2H_5)_2$ | H | H | $CH_3$ | H | CH | |
| $SO_2NHC_2H_5$ | H | H | $OCH_3$ | H | CH | |
| $SO_2N(CH_3)CH(CH_3)_2$ | H | H | $OCH_3$ | H | N | |

TABLE I-continued

General Structure I

| R₁ | R₂ | R | X | Y | Z | m.p. °C. |
|---|---|---|---|---|---|---|
| SO₂N(OCH₃)CH₃ | H | H | CH₃ | H | CH | |
| OSO₂CH₃ | H | H | OCH₃ | H | CH | |
| OSO₂CH₃ | H | H | OCH₃ | H | N | |
| OSO₂C₂H₅ | H | H | CH₃ | H | CH | |
| OSO₂(CH₂)₂CH₃ | H | H | OCH₃ | H | N | |
| OSO₂N(CH₃)₂ | H | H | OCH₃ | H | CH | |
| OCF₃ | H | H | CH₃ | H | CH | |
| SCF₃ | H | H | OCH₃ | H | N | |
| OCF₂H | H | H | OCH₃ | H | N | |
| SCF₂H | H | H | OCH₃ | H | CH | |
| SO₂CF₂H | H | H | CH₃ | H | CH | |
| OCH₂CH=CH₂ | H | H | OCH₃ | H | N | |
| OCH₂CH=CH₂ | H | H | OCH₃ | H | CH | |
| OCH₂C(CH₃)=CH₂ | H | H | CH₃ | H | CH | |
| OCH₂C(CH₃)=CH₂ | H | H | OCH₃ | H | N | |
| OCH₂C≡CH | H | H | OCH₃ | H | N | |
| OCH₂C≡CH | H | H | CH₃ | H | CH | |
| OCH₂C≡CCH₃ | H | H | OCH₃ | H | CH | |
| OCH₂C≡CCH₃ | H | H | CH₃ | H | CH | |
| CH₂OCH₃ | H | H | OCH₃ | H | N | |
| CH₂OCH₃ | H | H | CH₃ | H | CH | |
| (CH₂)₂OC₂H₅ | H | H | CH₃ | H | CH | |
| (CH₂)₂OC₂H₅ | H | H | OCH₃ | H | N | |
| C₆H₅ | H | H | OCH₃ | H | N | |
| C₆H₅ | H | H | OCH₃ | H | CH | |
| C≡CCH₃ | H | H | OCH | H | N | |
| C≡CCH₃ | H | H | OCH₃ | H | CH | |
| CH₂C≡CCH₃ | H | H | CH₃ | H | CH | |
| CH₂C≡CCH₃ | H | H | OCH₃ | H | N | |
| CH=CHCF₃ | H | H | OCH₃ | H | CH | |
| CH=CHCF₃ | H | H | OCH₃ | H | N | |
| CH=CHBr | H | H | CH₃ | H | CH | |
| CH=CHBr | H | H | OCH₃ | H | N | |
| Q-1 | H | H | OCH₃ | H | N | |
| Q-1 | H | H | OCH₃ | H | CH | |
| Q-2 | H | H | OCH₃ | H | N | |
| Q-2 | H | H | OCH₃ | H | CH | |
| Q-3 | H | H | OCH₃ | H | N | |
| Q-3 | H | H | OCH₃ | H | CH | |
| Q-4 | H | H | OCH₃ | H | N | |
| Q-4 | H | H | OCH₃ | H | CH | |
| Q-5 | H | H | OCH₃ | H | N | |
| Q-5 | H | H | OCH₃ | H | CH | |
| Q-6 | H | H | OCH₃ | H | N | |
| Q-6 | H | H | OCH₃ | H | CH | |
| Q-7 | H | H | OCH₃ | H | N | |
| Q-7 | H | H | OCH₃ | H | CH | |
| Q-8 | H | H | OCH₃ | H | N | |
| Q-8 | H | H | OCH₃ | H | CH | |
| Q-9 | H | H | OCH₃ | H | N | |
| Q-9 | H | H | OCH₃ | H | CH | |
| Q-10 | H | H | OCH₃ | H | N | |
| Q-10 | H | H | OCH₃ | H | CH | |
| Q-11 | H | H | OCH₃ | H | N | |
| Q-11 | H | H | OCH₃ | H | CH | |
| Q-12 | H | H | OCH₃ | H | N | |
| Q-12 | H | H | OCH₃ | H | CH | |
| Q-13 | H | H | OCH₃ | H | N | |
| Q-13 | H | H | OCH₃ | H | CH | |
| Q-14 | H | H | OCH₃ | H | N | |
| Q-14 | H | H | CH₃ | H | CH | |
| Q-15 | H | H | CH₃ | H | CH | |
| Q-15 | H | H | OCH₃ | H | N | |
| Q-16 | H | H | OCH₃ | H | N | |
| Q-16 | H | H | CH₃ | H | CH | |
| CO₂CH₃ | H | H | OCH₃ | (CH₂)₃CH₃ | CH | 134-136 |
| CO₂CH₃ | H | H | CH₃ | (CH₂)₃CH₃ | CH | 129-131 |
| CO₂CH₃ | H | H | OCH₃ | (CH₂)₃CH₃ | N | |
| *CO₂CH₃ | H | H | OCH₃ | H | CH | |
| CO₂CH₃ | H | H | CH₂CH₂CH₃ | H | CH | |
| CO₂CH₃ | H | H | OCH₂CH₂CH₃ | H | CH | |
| CO₂CH₃ | H | H | CH₂Br | H | CH | |
| CO₂CH₃ | H | H | OCH₂CH₂CH₂F | H | CH | |
| CO₂CH₃ | H | H | NHCH₃ | H | CH | |
| CO₂CH₃ | H | H | 1-cyclopropyl | H | CH | |
| CO₂CH₃ | H | H | CH₃ | Br | N | |
| CO₂CH₃ | H | H | CH₃ | I | N | |
| CO₂CH₃ | H | H | OCH₃ | 2-Cl—C₆H₄ | CH | |
| CO₂CH₃ | H | H | OCH₃ | 2-SCH₃—C₆H₄ | CH | |
| CO₂CH₃ | H | H | CH₃ | C(CH₃)₂OH | CH | 151-153°(d) |

TABLE I-continued

General Structure I

| $R_1$ | $R_2$ | R | X | Y | Z | m.p. °C. |
|---|---|---|---|---|---|---|
| $CO_2CH_3$ | H | H | $OCH_3$ | $C(CH_3)_2OH$ | CH | 156° |
| $CO_2CH_3$ | H | H | $N(CH_3)_2$ | $(CH_2)_3CH_3$ | CH | 168-169°(d) |
| $SO_2N(CH_3)_2$ | H | H | $N(CH_3)_2$ | $(CH_2)_3CH_3$ | CH | 166° |
| $CO_2CH_3$ | H | H | $CH_3$ | $C_6H_5$ | CH | 187-189° |
| $CO_2CH_2CH_3$ | H | H | $CH_3$ | $C_6H_5$ | CH | 184-188° |
| $SO_2N(CH_3)_2$ | H | H | $CH_3$ | $C_6H_5$ | CH | 179-185° |
| $CO_2CH_3$ | H | H | $OCH_3$ | $C_6H_5$ | CH | 195-197° |

*$W_1$ is sulfur

TABLE IA

General Structure I

| $R_1$ | $R_2$ | R | X | Y | Z | $R_{25}$ | m.p. °C. |
|---|---|---|---|---|---|---|---|
| Q-17 | H | H | $OCH_3$ | H | CH | H | |
| Q-17 | H | H | $CH_3$ | H | N | $CH_3$ | |
| Q-18 | H | H | $OCH_3$ | H | CH | H | |
| Q-18 | H | H | $CH_3$ | H | CH | $CH_3$ | |
| Q-19 | H | H | $OCH_3$ | H | N | H | |
| Q-19 | H | H | $OCH_3$ | $CH_3$ | CH | $CH_3$ | |
| Q-20 | H | H | $CH_3$ | $(CH_2)_3CH_3$ | CH | H | |
| Q-20 | H | H | $OCH_3$ | H | N | $CH_3$ | |

TABLE II

General Structure II

| $R_3$ | R | X | Y | Z |
|---|---|---|---|---|
| H | H | $CH_3$ | H | CH |
| H | H | $OCH_3$ | H | N |
| $CH_3$ | H | $CH_3$ | H | CH |
| $CH_3$ | H | $OCH_3$ | H | CH |
| $CH_3$ | H | $OCH_3$ | H | N |
| $OCH_3$ | H | $CH_3$ | H | CH |
| $OCH_3$ | H | $OCH_3$ | H | CH |
| $OCH_3$ | H | $OCH_3$ | H | N |
| F | H | $OCH_3$ | H | CH |
| Cl | H | $CH_3$ | H | CH |
| Cl | H | $OCH_3$ | H | CH |
| Cl | H | $OCH_3$ | H | N |
| Cl | H | $CH_3$ | H | N |
| Cl | H | $OCH_3$ | $CH_3$ | CH |
| Cl | H | $CH_3$ | $C_2H_5$ | CH |
| Cl | H | $OCH_3$ | $(CH_2)_2CH_3$ | CH |
| Cl | $CH_3$ | $OCH_3$ | H | CH |
| Br | H | $CH_3$ | H | CH |
| Br | H | $OCH_3$ | H | CH |
| Br | H | $OCH_3$ | H | N |
| $SO_2N(CH_3)_2$ | H | $CH_3$ | H | CH |
| $SO_2N(CH_3)_2$ | H | $OCH_3$ | H | CH |
| $SO_2N(CH_3)_2$ | H | $OCH_3$ | H | N |
| $OSO_2CH_3$ | H | $OCH_3$ | H | CH |
| $OSO_2CH_3$ | H | $OCH_3$ | H | N |
| $OSO_2CH_3$ | H | $CH_3$ | H | CH |
| $SCH_3$ | H | $OCH_3$ | H | N |
| $SCH_3$ | H | $CH_3$ | H | CH |
| $SCH_3$ | H | $OCH_3$ | H | CH |
| $SO_2CH_3$ | H | $OCH_3$ | H | N |
| $SO_2CH_3$ | H | $OCH_3$ | H | CH |
| $SO_2CH_3$ | H | $CH_3$ | H | CH |
| $SO_2CH_3$ | H | $OCH_3$ | $(CH_2)_3CH_3$ | CH |
| $SO_2CH_3$ | H | $CH_3$ | $(CH_2)_3CH_3$ | CH |

TABLE III

General Structure III

| $R_4$ | R | X | Y | Z |
|---|---|---|---|---|
| $CH_3$ | H | $CH_3$ | H | CH |
| $CH_3$ | H | $OCH_3$ | H | CH |
| $CH_3$ | H | $OCH_3$ | H | N |
| $CH_3$ | H | $CH_3$ | H | N |
| $C_2H_5$ | H | $OCH_3$ | H | CH |
| $C_2H_5$ | H | $OCH_3$ | H | N |
| $C_2H_5$ | H | $CH_3$ | H | CH |
| $OCH_3$ | H | $CH_3$ | H | CH |
| $OCH_3$ | H | $OCH_3$ | H | CH |

TABLE III-continued

General Structure III

| $R_4$ | R | X | Y | Z |
|---|---|---|---|---|
| $OCH_3$ | H | $OCH_3$ | H | N |
| $OCH_3$ | H | $CH_3$ | H | N |
| $OC_2H_5$ | H | $OCH_3$ | H | CH |
| $OC_2H_5$ | H | $OCH_3$ | H | N |
| F | H | $CH_3$ | H | CH |
| F | H | $OCH_3$ | H | CH |
| Cl | H | $CH_3$ | H | CH |
| Cl | H | $OCH_3$ | H | N |
| Cl | H | $OCH_3$ | H | CH |
| Cl | H | $CH_3$ | H | N |
| Cl | H | $OCH_3$ | $CH_3$ | N |
| Cl | H | $OCH_3$ | $C_2H_5$ | CH |
| Cl | H | $OCH_3$ | $(CH_2)_2CH_3$ | CH |
| Cl | $CH_3$ | $OCH_3$ | H | N |
| Br | H | $CH_3$ | H | CH |
| Br | H | $OCH_3$ | H | CH |
| Br | H | $OCH_3$ | H | N |
| $SO_2N(CH_3)_2$ | H | $CH_3$ | H | CH |
| $SO_2N(CH_3)_2$ | H | $OCH_3$ | H | CH |
| $SO_2N(CH_3)_2$ | H | $OCH_3$ | H | N |
| $SO_2N(CH_3)_2$ | H | $CH_3$ | H | N |
| $SO_2NHCH_3$ | H | $OCH_3$ | H | CH |
| $SO_2N(C_2H_5)_2$ | H | $OCH_3$ | H | N |
| $SO_2N(CH_3)(CH_2)_2CH_3$ | H | $CH_3$ | H | CH |
| $SO_2N(OCH_3)CH_3$ | H | $CH_3$ | H | CH |
| $SO_2N(OCH_3)CH_3$ | H | $OCH_3$ | H | CH |
| $SO_2N(OCH_3)CH_3$ | H | $OCH_3$ | H | N |
| $SCH_3$ | H | $OCH_3$ | H | N |
| $SO_2CH_3$ | H | $CH_3$ | H | CH |
| $SO_2CH_3$ | H | $OCH_3$ | H | N |
| $SO_2CH_3$ | H | $OCH_3$ | H | CH |
| $SC_2H_5$ | H | $CH_3$ | H | CH |
| $SO_2C_2H_5$ | H | $OCH_3$ | H | N |
| $SO_2C_2H_5$ | N | $OCH_3$ | H | N |
| $S(CH_2)_2CH_3$ | H | $OCH_3$ | H | CH |
| $SO_2(CH_2)_2CH_3$ | H | $OCH_3$ | H | N |
| $SCH_2CH=CH_2$ | H | $CH_3$ | H | CH |
| $SO_2CH_2CH=CH_2$ | H | $OCH_3$ | H | CH |
| $SO_2CH_2CH=CH_2$ | H | $OCH_3$ | H | N |
| $OCH_2CH=CH_2$ | H | $CH_3$ | H | CH |
| $OCH_2CH=CH_2$ | H | $OCH_3$ | H | CH |
| $OCH_2CH=CH_2$ | H | $OCH_3$ | H | N |
| $OCH(CH_3)=CH_2$ | H | $CH_3$ | H | CH |
| $OCH(CH_3)=CH_2$ | H | $OCH_3$ | H | N |
| $OCH(CH_3)=CH_2$ | H | $OCH_3$ | H | N |
| $CH_2OCH_3$ | H | $CH_3$ | H | N |
| $CH_2OCH_3$ | H | $OCH_3$ | H | N |
| $CH_2OCH_3$ | H | $OCH_3$ | H | CH |
| $CH_2OCH_3$ | H | $CH_3$ | H | CH |
| $CH_2OC_2H_5$ | H | $CH_3$ | H | CH |
| $CH_2OC_2H_5$ | H | $OCH_3$ | H | CH |
| $CH_2OC_2H_5$ | H | $OCH_3$ | H | N |
| $SO_2N(CH_3)_2$ | H | $OCH_3$ | $(CH_2)_3CH_3$ | CH |

TABLE IV

General Structure IV

| L | $R_5$ | R | X | Y | Z |
|---|---|---|---|---|---|
| L-4 | $CO_2CH_3$ | H | $CH_3$ | H | CH |
| L-4 | $CO_2CH_3$ | H | $OCH_3$ | H | N |
| L-4 | $CO_2CH_3$ | H | $OCH_3$ | H | CH |
| L-4 | $CO_2CH_3$ | H | $CH_3$ | H | N |
| L-4 | $CO_2CH_3$ | H | $OCH_3$ | $CH_3$ | N |

TABLE IV-continued

General Structure IV

| L | R₅ | R | X | Y | Z |
|---|---|---|---|---|---|
| L-4 | CO₂CH₃ | H | OCH₃ | C₂H₅ | CH |
| L-4 | CO₂CH₃ | H | OCH₃ | (CH₂)₂CH₃ | CH |
| L-4 | CO₂C₂H₅ | H | OCH₃ | H | CH |
| L-4 | CO₂C₂H₅ | H | CH₃ | H | CH |
| L-4 | CO₂C₂H₅ | H | OCH₃ | H | N |
| L-4 | CO₂(CH₂)₂CH₃ | H | OCH₃ | H | CH |
| L-4 | CO₂(CH₂)₂CH₃ | H | OCH₃ | H | N |
| L-4 | CO₂(CH₂)₂OCH₃ | H | CH₃ | H | CH |
| L-4 | CO₂CH₂CH=CH₂ | H | OCH₃ | H | N |
| L-4 | CO₂(CH₂)₂Cl | H | OCH₃ | H | CH |
| L-4 | CH₃ | H | CH₃ | H | CH |
| L-4 | CH₃ | H | OCH₃ | H | N |
| L-4 | CH₃ | H | OCH₃ | H | CH |
| L-4 | C₂H₅ | H | OCH₃ | H | CH |
| L-4 | (CH₂)₂CH₃ | H | OCH₃ | H | CH |
| L-4 | Cl | H | CH₃ | H | CH |
| L-4 | Cl | H | OCH₃ | H | N |
| L-4 | Cl | H | OCH₃ | H | CH |
| L-4 | F | H | OCH₃ | H | CH |
| L-4 | Br | H | CH₃ | H | CH |
| L-4 | Br | H | OCH₃ | H | N |
| L-4 | Br | H | OCH₃ | H | CH |
| L-4 | NO₂ | H | CH₃ | H | N |
| L-4 | NO₂ | H | OCH₃ | H | N |
| L-4 | NO₂ | H | OCH₃ | H | CH |
| L-4 | NO₂ | H | CH₃ | H | CH |
| L-4 | SO₂N(CH₃)₂ | H | CH₃ | H | N |
| L-4 | SO₂N(CH₃)₂ | H | OCH₃ | H | N |
| L-4 | SO₂N(CH₃)₂ | H | OCH₃ | H | CH |
| L-4 | SO₂N(CH₃)₂ | H | CH₃ | H | CH |
| L-4 | SO₂N(CH₃)C₂H₅ | H | OCH₃ | H | N |
| L-4 | SO₂NHC₂H₅ | H | OCH₃ | H | CH |
| L-4 | SO₂NHCH(CH₃)₂ | H | OCH₃ | H | CH |
| L-4 | SO₂N(OCH₃)CH₃ | H | OCH₃ | H | N |
| L-4 | SO₂N(OCH₃)CH₃ | H | CH₃ | H | CH |
| L-4 | SO₂N(OCH₃)CH₃ | H | OCH₃ | H | CH |
| L-4 | SCH₃ | H | CH₃ | H | CH |
| L-4 | SCH₃ | H | OCH₃ | H | CH |
| L-4 | SCH₃ | H | OCH₃ | H | N |
| L-4 | SO₂CH₃ | H | CH₃ | H | N |
| L-4 | SO₂CH₃ | H | OCH₃ | H | N |
| L-4 | SO₂CH₃ | H | OCH₃ | H | CH |
| L-4 | SO₂CH₃ | H | CH₃ | H | CH |
| L-4 | SC₂H₅ | H | OCH₃ | H | N |
| L-4 | SC₂H₅ | H | OCH₃ | H | CH |
| L-4 | SC₂H₅ | H | CH₃ | H | CH |
| L-4 | SO₂C₂H₅ | H | CH₃ | H | CH |
| L-4 | SO₂C₂H₅ | H | OCH₃ | H | N |
| L-4 | SO₂C₂H₅ | H | OCH₃ | H | CH |
| L-4 | S(CH₂)₂CH₃ | H | OCH₃ | H | N |
| L-4 | SO₂(CH₂)₂CH₃ | H | OCH₃ | H | CH |
| L-4 | SCH₂CH=CH₂ | H | OCH₃ | H | N |
| L-4 | SO₂CH₂CH=CH₂ | H | OCH₃ | H | CH |
| L-4 | CO₂CH₃ | CH₃ | OCH₃ | H | CH |
| L-4 | SO₂N(CH₃)₂ | CH₃ | OCH₃ | H | CH |
| L-4 | SO₂CH₃ | CH₃ | OCH₃ | H | CH |
| L-4 | NO₂ | CH₃ | OCH₃ | H | CH |
| L-4 | Cl | CH₃ | OCH₃ | H | CH |
| L-4 | CH₃ | CH₃ | OCH₃ | H | CH |
| L-4 | CO₂CH₃ | H | OCH₃ | (CH₂)₃CH₃ | CH |
| L-4 | CO₂CH₃ | H | OCH₃ | (CH₂)₃CH₃ | N |
| L-4 | SO₂N(CH₃)₂ | H | OCH₃ | (CH₂)₃CH₃ | CH |

TABLE IVA

General Structure IVA

| L | R₅ | R | X | Y | Z | m.p. °C. |
|---|---|---|---|---|---|---|
| L-5 | CO₂CH₃ | H | CH₃ | H | CH | |
| L-5 | CO₂CH₃ | H | OCH₃ | H | N | 176–179 |
| L-5 | CO₂CH₃ | H | OCH₃ | H | CH | |
| L-5 | CO₂CH₃ | H | CH₃ | H | N | |
| L-5 | CO₂CH₃ | H | OCH₃ | CH₃ | N | |
| L-5 | CO₂CH₃ | H | OCH₃ | C₂H₅ | CH | |
| L-5 | CO₂CH₃ | H | OCH₃ | H | CH | |
| L-5 | CO₂C₂H₅ | H | CH₃ | H | CH | |
| L-5 | CO₂C₂H₅ | H | OCH₃ | H | N | |
| L-5 | CO₂(CH₂)₂CH₃ | H | OCH₃ | H | CH | |
| L-5 | CO₂(CH₂)₃CH₃ | H | OCH₃ | H | N | |

TABLE IVA-continued

General Structure IVA

| L | R₅ | R | X | Y | Z | m.p. °C. |
|---|---|---|---|---|---|---|
| L-5 | CO₂(CH₂)₂OCH₃ | H | CH₃ | H | CH | |
| L-5 | CO₂CH₂CH=CH₂ | H | OCH₃ | H | N | |
| L-5 | CO₂(CH₂)₂Cl | H | OCH₃ | H | CH | |
| L-5 | CH₃ | H | CH₃ | H | CH | |
| L-5 | CH₃ | H | OCH₃ | H | N | |
| L-5 | CH₃ | H | OCH₃ | H | CH | |
| L-5 | C₂H₅ | H | CH₃ | H | CH | |
| L-5 | (CH₂)₂CH₃ | H | OCH₃ | H | CH | |
| L-5 | Cl | H | CH₃ | H | CH | |
| L-5 | Cl | H | OCH₃ | H | N | |
| L-5 | Cl | H | OCH₃ | H | CH | |
| L-5 | F | H | OCH₃ | H | CH | |
| L-5 | Br | H | CH₃ | H | CH | |
| L-5 | Br | H | OCH₃ | H | N | |
| L-5 | Br | H | OCH₃ | H | CH | |
| L-5 | NO₂ | H | CH₃ | H | N | |
| L-5 | NO₂ | H | OCH₃ | H | N | |
| L-5 | NO₂ | H | OCH₃ | H | CH | |
| L-5 | SO₂N(CH₃)₂ | H | CH₃ | H | N | |
| L-5 | SO₂N(CH₃)₂ | H | OCH₃ | H | N | |
| L-5 | SO₂N(CH₃)₂ | H | CH₃ | H | CH | |
| L-5 | SO₂N(CH₃)C₂H₅ | H | OCH₃ | H | N | |
| L-5 | SO₂NHC₂H₅ | H | OCH₃ | H | CH | |
| L-5 | SO₂NHCH(CH₃)₂ | H | OCH₃ | H | CH | |
| L-5 | SO₂N(OCH₃)CH₃ | H | OCH₃ | H | N | |
| L-5 | SO₂N(OCH₃)CH₃ | H | CH₃ | H | CH | |
| L-5 | SO₂N(OCH₃)CH₃ | H | OCH₃ | H | CH | |
| L-5 | SCH₃ | H | CH₃ | H | CH | |
| L-5 | SCH₃ | H | OCH₃ | H | CH | |
| L-5 | SCH₃ | H | OCH₃ | H | N | |
| L-5 | SO₂CH₃ | H | CH₃ | H | N | |
| L-5 | SO₂CH₃ | H | OCH₃ | H | N | |
| L-5 | SO₂CH₃ | H | OCH₃ | H | CH | |
| L-5 | SO₂CH₃ | H | CH₃ | H | CH | |
| L-5 | SC₂H₅ | H | OCH₃ | H | N | |
| L-5 | SC₂H₅ | H | OCH₃ | H | CH | |
| L-5 | SC₂H₅ | H | CH₃ | H | CH | |
| L-5 | SO₂C₂H₅ | H | CH₃ | H | CH | |
| L-5 | SO₂C₂H₅ | H | OCH₃ | H | N | |
| L-5 | SO₂C₂H₅ | H | OCH₃ | H | CH | |
| L-5 | S(CH₂)₂CH₃ | H | OCH₃ | H | N | |
| L-5 | SO₂(CH₂)₂CH₃ | H | OCH₃ | H | CH | |
| L-5 | SCH₂CH=CH₂ | H | OCH₃ | H | N | |
| L-5 | SO₂CH₂CH=CH₂ | H | OCH₃ | H | CH | |
| L-5 | CO₂CH₃ | CH₃ | OCH₃ | H | CH | |
| L-5 | SO₂N(CH₃)₂ | CH₃ | OCH₃ | H | CH | |
| L-5 | SO₂CH₃ | CH₃ | OCH₃ | H | CH | |
| L-5 | NO₂ | CH₃ | OCH₃ | H | CH | |
| L-5 | Cl | CH₃ | OCH₃ | H | CH | |
| L-5 | CH₃ | CH₃ | OCH₃ | H | CH | |
| L-5 | CO₂CH₃ | H | CH₃ | C₆H₅ | CH | 187–189° |
| L-5 | CO₂CH₃ | H | OCH₃ | C₆H₅ | CH | 123–125° |
| L-5 | CO₂CH₃ | H | OCH₃ | H | CH | 182–184° (d) |

TABLE IVB

General Structure IVB

| L | R₅ | R | X | Y | Z |
|---|---|---|---|---|---|
| L-6 | CO₂CH₃ | H | CH₃ | H | CH |
| L-6 | CO₂CH₃ | H | OCH₃ | H | N |
| L-6 | CO₂CH₃ | H | OCH₃ | H | CH |
| L-6 | CO₂CH₃ | H | CH₃ | H | N |
| L-6 | CO₂CH₃ | H | OCH₃ | CH₃ | N |
| L-6 | CO₂CH₃ | H | OCH₃ | C₂H₅ | CH |
| L-6 | CO₂CH₃ | H | OCH₃ | (CH₂)₃CH₃ | CH |
| L-6 | CO₂C₂H₅ | H | OCH₃ | H | CH |
| L-6 | CO₂C₂H₅ | H | CH₃ | H | CH |
| L-6 | CO₂C₂H₅ | H | OCH₃ | H | N |
| L-6 | CO₂(CH₂)₂CH₃ | H | OCH₃ | H | CH |
| L-6 | CO₂(CH₂)₃CH₃ | H | OCH₃ | H | N |
| L-6 | CO₂(CH₂)₂OCH₃ | H | CH₃ | H | CH |
| L-6 | CO₂CH₂CH=CH₂ | H | OCH₃ | H | N |
| L-6 | CO₂(CH₂)₂Cl | H | OCH₃ | H | CH |
| L-6 | CH₃ | H | CH₃ | H | CH |
| L-6 | CH₃ | H | OCH₃ | H | N |

TABLE IVB-continued

General Structure IVB

| L | R₅ | R | X | Y | Z |
|---|---|---|---|---|---|
| L-6 | CH₃ | H | OCH₃ | H | CH |
| L-6 | C₂H₅ | H | CH₃ | H | CH |
| L-6 | (CH₂)₂CH₃ | H | OCH₃ | H | CH |
| L-6 | Cl | H | CH₃ | H | CH |
| L-6 | Cl | H | OCH₃ | H | N |
| L-6 | Cl | H | OCH₃ | H | CH |
| L-6 | F | H | OCH₃ | H | CH |
| L-6 | Br | H | CH₃ | H | CH |
| L-6 | Br | H | OCH₃ | H | N |
| L-6 | Br | H | OCH₃ | H | CH |
| L-6 | NO₂ | H | CH₃ | H | N |
| L-6 | NO₂ | H | OCH₃ | H | N |
| L-6 | NO₂ | H | OCH₃ | H | CH |
| L-6 | NO₂ | H | CH₃ | H | CH |
| L-6 | SO₂N(CH₃)₂ | H | CH₃ | H | N |
| L-6 | SO₂N(CH₃)₂ | H | OCH₃ | H | N |
| L-6 | SO₂N(CH₃)₂ | H | OCH₃ | H | CH |
| L-6 | SO₂N(CH₃)₂ | H | CH₃ | H | CH |
| L-6 | SO₂N(CH₃)C₂H₅ | H | OCH₃ | H | N |
| L-6 | SO₂NHC₂H₅ | H | OCH₃ | H | CH |
| L-6 | SO₂NHCH(CH₃)₂ | H | OCH₃ | H | CH |
| L-6 | SO₂N(OCH₃)CH₃ | H | OCH₃ | H | N |
| L-6 | SO₂N(OCH₃)CH₃ | H | CH₃ | H | CH |
| L-6 | SO₂N(OCH₃)CH₃ | H | OCH₃ | H | CH |
| L-6 | SCH₃ | H | CH₃ | H | CH |
| L-6 | SCH₃ | H | OCH₃ | H | CH |
| L-6 | SCH₃ | H | OCH₃ | H | N |
| L-6 | SO₂CH₃ | H | CH₃ | H | N |
| L-6 | SO₂CH₃ | H | OCH₃ | H | N |
| L-6 | SO₂CH₃ | H | OCH₃ | H | CH |
| L-6 | SO₂CH₃ | H | CH₃ | H | CH |
| L-6 | SC₂H₅ | H | OCH₃ | H | N |
| L-6 | SC₂H₅ | H | OCH₃ | H | CH |
| L-6 | SC₂H₅ | H | CH₃ | H | CH |
| L-6 | SO₂C₂H₅ | H | CH₃ | H | CH |
| L-6 | SO₂C₂H₅ | H | OCH₃ | H | N |
| L-6 | SO₂C₂H₅ | H | OCH₃ | H | CH |
| L-6 | S(CH₂)₂CH₃ | H | OCH₃ | H | N |
| L-6 | SO₂(CH₂)₂CH₃ | H | OCH₃ | H | CH |
| L-6 | SCH₂CH=CH₂ | H | OCH₃ | H | N |
| L-6 | SO₂CH₂CH=CH₂ | H | OCH₃ | H | CH |
| L-6 | CO₂CH₃ | CH₃ | OCH₃ | H | CH |
| L-6 | SO₂N(CH₃)₂ | CH₃ | OCH₃ | H | CH |
| L-6 | SO₂CH₃ | CH₃ | OCH₃ | H | CH |
| L-6 | NO₂ | | CH₃ | OCH₃ | H | CH |
| L-6 | Cl | | CH₃ | OCH₃ | H | CH |
| L-6 | CH₃ | | CH₃ | OCH₃ | H | CH |
| L-6 | CO₂CH₃ | | H | OCH₃ | (CH₂)₃CH₃ | CH |

TABLE V

General Structure V

| R₆ | R | X | Y | Z |
|---|---|---|---|---|
| Cl | H | OCH₃ | H | CH |
| NO₂ | H | OCH₃ | H | CH |
| NO₂ | H | OCH₃ | H | N |
| CO₂CH₃ | H | CH₃ | H | CH |
| CO₂CH₃ | H | OCH₃ | H | CH |
| CO₂CH₃ | H | OCH₃ | H | N |
| CO₂CH₃ | H | CH₃ | H | N |
| CO₂CH₃ | H | OCH₃ | CH₃ | CH |
| CO₂CH₃ | H | OCH₃ | C₂H₅ | CH |
| CO₂CH₃ | H | OCH₃ | (CH₂)₃CH₃ | CH |
| CO₂C₂H₅ | H | CH₃ | H | CH |
| CO₂C₂H₅ | H | OCH₃ | H | CH |
| CO₂C₂H₅ | H | OCH₃ | H | N |
| SO₂N(CH₃)₂ | H | CH₃ | H | CH |
| SO₂N(CH₃)₂ | H | OCH₃ | H | N |
| SO₂N(CH₃)₂ | H | OCH₃ | H | CH |
| OSO₂CH₃ | H | OCH₃ | H | N |
| OSO₂CH₃ | H | CH₃ | H | CH |
| OSO₂CH₃ | H | OCH₃ | H | CH |
| SO₂CH₃ | H | OCH₃ | H | N |
| SO₂CH₃ | H | OCH₃ | H | CH |
| SO₂CH₃ | H | CH₃ | H | CH |
| SO₂C₂H₅ | H | CH₃ | H | CH |
| SO₂C₂H₅ | H | OCH₃ | H | N |
| SO₂C₂H₅ | H | OCH₃ | H | CH |
| OCH₃ | H | OCH₃ | H | N |
| OCH₃ | H | CH₃ | H | CH |
| OCH₃ | H | OCH₃ | H | CH |
| OC₂H₅ | H | OCH₃ | H | CH |
| OC₂H₅ | H | CH₃ | H | CH |
| OC₂H₅ | H | OCH₃ | H | N |
| CO₂CH₃ | CH₃ | OCH₃ | H | CH |
| CO₂CH₃ | H | OCH₃ | (CH₂)₃CH₃ | N |

TABLE VI

General Structure VI

| R₇ | R₈ | Q₁ | R₉ | m | R₂ | R | X | Y | Z | m.p. °C. |
|---|---|---|---|---|---|---|---|---|---|---|
| H | H | O | H | 0 | H | H | CH₃ | H | CH | |
| H | H | O | H | 0 | H | H | OCH₃ | H | CH | |
| H | H | O | H | 0 | H | H | OCH₃ | H | N | |
| H | H | O | H | 0 | H | H | CH₃ | H | N | |
| H | H | O | H | 1 | H | H | CH₃ | H | N | |
| H | H | O | H | 1 | H | H | OCH₃ | H | N | |
| H | H | O | H | 1 | H | H | OCH₃ | H | CH | |
| H | H | O | CH₃ | 0 | H | H | CH₃ | H | CH | |
| CH₃ | H | O | H | 0 | H | H | CH₃ | H | CH | |
| CH₃ | H | O | H | 0 | H | H | CH₃ | H | N | |
| CH₃ | H | O | H | 0 | H | H | OCH₃ | H | N | |
| CH₃ | CH₃ | O | H | 0 | H | H | OCH₃ | H | N | |
| CH₃ | CH₃ | O | H | 0 | H | H | OCH₃ | H | CH | |
| C₂H₅ | H | O | H | 0 | H | H | CH₃ | H | CH | |
| H | C₂H₅ | O | H | 0 | H | H | OCH₃ | H | N | |
| CH₃ | H | O | H | 1 | H | H | OCH₃ | H | N | |
| CH₃ | H | O | H | 1 | H | H | CH₃ | H | CH | |
| CH₃ | H | O | H | 1 | H | H | OCH₃ | H | CH | |
| C₂H₅ | H | O | H | 1 | H | H | OCH₃ | H | N | |
| C₂H₅ | H | O | H | 1 | H | H | OCH₃ | H | CH | |
| H | H | S | H | 0 | H | H | CH₃ | H | CH | |
| H | H | S | H | 0 | H | H | OCH₃ | H | CH | |
| H | H | S | H | 0 | H | H | OCH₃ | H | N | |
| CH₃ | H | S | H | 0 | H | H | OCH₃ | H | N | |
| CH₃ | H | S | H | 0 | H | H | OCH₃ | H | CH | |
| CH₃ | H | S | H | 0 | H | H | CH₃ | H | CH | |
| CH₃ | CH₃ | S | H | 0 | H | H | OCH₃ | H | CH | |
| H | C₂H₅ | S | H | 0 | H | H | OCH₃ | H | CH | |
| H | C₂H₅ | S | H | 0 | H | H | OCH₃ | (CH₂)₄CH₃ | CH | |

TABLE VI-continued

General Structure VI

| R$_7$ | R$_8$ | Q$_1$ | R$_9$ | m | R$_2$ | R | X | Y | Z | m.p. °C. |
|---|---|---|---|---|---|---|---|---|---|---|
| H | H | SO$_2$ | H | 0 | H | H | OCH$_3$ | H | N | |
| H | H | SO$_2$ | H | 0 | H | H | CH$_3$ | H | CH | |
| H | H | SO$_2$ | H | 0 | H | H | OCH$_3$ | H | CH | |
| CH$_3$ | H | SO$_2$ | H | 0 | H | H | CH$_3$ | H | CH | |
| CH$_3$ | H | SO$_2$ | H | 0 | H | H | OCH$_3$ | H | N | |
| CH$_3$ | H | SO$_2$ | H | 0 | H | H | OCH$_3$ | H | CH | |
| C$_2$H$_5$ | H | SO$_2$ | H | 0 | H | H | OCH$_3$ | H | N | |
| C$_2$H$_5$ | H | SO$_2$ | H | 0 | H | H | OCH$_3$ | H | CH | |
| C$_2$H$_5$ | H | SO$_2$ | H | 0 | H | H | CH$_3$ | H | CH | |
| H | H | SO$_2$ | H | 0 | 7-Cl | CH$_3$ | OCH$_3$ | H | CH | |
| CH$_3$ | H | NH | H | 1 | H | H | OCH$_3$ | H | CH | |
| CH$_3$ | H | NCH$_3$ | H | 1 | H | H | OCH$_3$ | H | CH | |
| CH$_3$ | CH$_3$ | SO$_2$ | H | 0 | H | H | OCH$_3$ | H | N | 149–150 (d) |
| H | H | SO$_2$ | H | 0 | H | H | OCH$_3$ | (CH$_2$)$_3$CH$_3$ | CH | |
| CH$_3$ | CH$_3$ | O | H | 0 | H | H | OCH$_3$ | (CH$_2$)$_4$CH$_3$ | N | |

TABLE VII

General Structure VII

| Q$_2$ | R$_{10}$ | R$_{11}$ | R$_2$ | R | X | Y | Z |
|---|---|---|---|---|---|---|---|
| O | H | H | H | H | CH$_3$ | H | CH |
| O | H | H | H | H | OCH$_3$ | H | N |
| O | H | H | H | H | CH$_3$ | H | CH |
| O | H | H | H | H | OCH$_3$ | H | N |
| O | CH$_3$ | H | H | H | CH$_3$ | H | CH |
| O | CH$_3$ | H | H | H | OCH$_3$ | H | N |
| O | CH$_3$ | H | H | H | OCH$_3$ | H | N |
| O | CH$_3$ | CH$_3$ | H | H | OCH$_3$ | H | CH |
| O | CH$_3$ | CH$_3$ | H | H | OCH$_3$ | H | N |
| O | CH$_3$ | CH$_3$ | H | CH$_3$ | OCH$_3$ | H | N |
| S | H | H | 5-Cl | H | CH$_3$ | H | CH |
| S | H | H | H | H | OCH$_3$ | H | N |
| S | H | H | H | H | OCH$_3$ | H | N |
| S | CH$_3$ | H | H | H | OCH$_3$ | H | CH |
| S | CH$_3$ | H | H | H | OCH$_3$ | H | N |
| S | CH$_3$ | H | H | H | CH$_3$ | H | CH |
| S | H | CH$_3$ | H | H | OCH$_3$ | H | N |
| S | H | CH$_3$ | H | H | OCH$_3$ | H | CH |
| S | H | H | H | H | OCH$_3$ | (CH$_2$)$_3$CH$_3$ | CH |

TABLE VIII

General Structure VIII

| L | R | R$_2$ | R$_9$ | m | X | Y | Z | R$_{23}$ | R$_{24}$ |
|---|---|---|---|---|---|---|---|---|---|
| L-11 | H | H | H | 0 | CH$_3$ | H | CH | | |
| L-11 | H | H | H | 0 | OCH$_3$ | H | N | | |
| L-11 | H | H | H | 0 | OCH$_3$ | H | CH | | |
| L-11 | H | H | H | 0 | CH$_3$ | H | N | | |
| L-11 | H | H | H | 0 | OCH$_3$ | CH$_3$ | CH | | |
| L-11 | H | H | H | 0 | OCH$_3$ | C$_2$H$_5$ | CH | | |
| L-11 | H | H | H | 0 | OCH$_3$ | (CH$_2$)$_2$CH$_3$ | CH | | |
| L-11 | H | H | H | 0 | OCH$_3$ | (CH$_2$)$_3$CH$_3$ | CH | | |
| L-11 | H | H | H | 1 | CH$_3$ | H | N | | |
| L-11 | H | H | H | 1 | OCH$_3$ | H | N | | |
| L-11 | H | H | H | 1 | OCH$_3$ | H | CH | | |
| L-11 | H | H | H | 0 | CH$_3$ | CH$_3$ | CH | | |
| L-11 | H | H | H | 0 | OCH$_3$ | CH$_3$ | N | | |
| L-11 | H | H | H | 0 | OCH$_2$CH$_3$ | CH$_3$ | CH | | |
| L-11 | H | m-Cl | H | 0 | CH$_3$ | H | CH | | |
| L-11 | H | m-Cl | H | 0 | OCH$_3$ | H | N | | |
| L-11 | H | m-Cl | H | 0 | OCH$_3$ | H | CH | | |
| L-11 | H | m-CF$_3$ | H | 0 | OCH$_3$ | H | N | | |
| L-11 | H | m-OCH$_3$ | H | 0 | CH$_3$ | H | CH | | |
| L-11 | H | m-OCH$_3$ | H | 0 | OCH$_3$ | H | N | | |
| L-11 | H | m-OCH$_3$ | H | 0 | OCH$_3$ | H | CH | | |
| L-11 | H | m-F | H | 1 | OCH$_3$ | H | CH | | |
| L-11 | H | m-F | H | 1 | OCH$_3$ | H | N | | |
| L-11 | H | o-Br | H | 1 | OCH$_3$ | H | N | | |
| L-11 | H | H | CH$_3$ | 0 | OCH$_3$ | H | CH | | |
| L-11 | H | H | CH$_3$ | 0 | OCH$_3$ | H | N | | |
| L-11 | CH$_3$ | H | H | 0 | OCH$_3$ | H | N | | |
| L-11 | CH$_3$ | H | H | 1 | OCH$_3$ | H | CH | | |
| L-12* | H | H | CH$_3$ | 0 | OCH$_3$ | H | N | | |
| L-12 | H | H | H | 0 | OCH$_3$ | H | CH | | |
| L-12 | H | H | H | 0 | CH$_3$ | H | CH | | |
| L-12 | H | H | H | 1 | OCH$_3$ | H | CH | — | — |
| L-12 | H | H | H | 1 | OCH$_3$ | H | N | — | — |
| L-12 | H | H | H | 1 | CH$_3$ | H | CH | — | — |
| L-12 | H | H | H | 1 | OCH$_3$ | H | N | | |
| L-13 | H | H | CH$_3$ | 0 | OCH$_3$ | H | CH | H | H |
| L-13 | H | H | H | 0 | CH$_3$ | H | CH | H | H |
| L-13 | H | H | H | 0 | OCH$_3$ | H | N | Cl | Cl |
| L-13 | H | H | H | 0 | OCH$_3$ | H | CH | Cl | Cl |
| L-13 | H | H | H | 1 | CH$_3$ | H | CH | Cl | Cl |
| L-13 | H | H | H | 1 | OCH$_3$ | H | N | H | H |
| L-13 | H | H | H | 1 | OCH$_3$ | H | CH | H | H |

TABLE VIII-continued

General Structure VIII

| L | R | $R_2$ | $R_9$ | m | X | Y | Z | $R_{23}$ | $R_{24}$ |
|---|---|---|---|---|---|---|---|---|---|
| L-11 | H | H | H | 0 | $OCH_3$ | $(CH_2)_3CH_3$ | CH | — | — |
| L-12 | H | H | H | 0 | $OCH_3$ | $(CH_2)_3CH_3$ | CH | — | — |
| L-13 | H | H | H | 0 | $OCH_3$ | $(CH_2)_3CH_3$ | N | H | H |

*$Q_3$ is S; otherwise $Q_3$ is $NCH_3$.

TABLE IX

General Structure IX

| $R_{12}$ | $R_2$ | R | X | Y | Z |
|---|---|---|---|---|---|
| H | H | H | $OCH_3$ | H | CH |
| $CH_3$ | H | H | $OCH_3$ | H | CH |
| $C_2H_5$ | H | H | $OCH_3$ | H | CH |
| $CH(CH_3)_2$ | H | H | $OCH_3$ | H | CH |
| $(CH_2)_3CH_3$ | H | H | $OCH_3$ | H | CH |
| $CH_2CH=CH_2$ | H | H | $OCH_3$ | H | CH |
| $CH_2CH_2OCH_3$ | H | H | $OCH_3$ | H | CH |
| $CH_2CH(OCH_3)CH_3$ | H | H | $OCH_3$ | H | CH |
| $CH_2C\equiv CH$ | H | H | $OCH_3$ | H | CH |
| $CH_2C(CH_3)=CH_2$ | H | H | $OCH_3$ | H | CH |
| $CH_2C_6H_5$ | H | H | $OCH_3$ | H | CH |
| $CH_2CH_2F$ | H | H | $OCH_3$ | H | CH |
| $CH_2CH_2Cl$ | H | H | $OCH_3$ | H | CH |
| $CH_3$ | H | H | $OCH_3$ | H | N |
| $CH_2CH_3$ | H | H | $OCH_3$ | H | N |
| $CH_2CH_2F$ | H | H | $OCH_3$ | H | N |
| $CH_2CH_2OCH_3$ | H | H | $OCH_3$ | H | N |
| $CH_3$ | H | H | $OCH_3$ | $(CH_2)_3CH_3$ | CH |

TABLE X

General Structure X

| $R_{12}$ | $R_9$ | R | $R_2$ | m | X | Y | Z |
|---|---|---|---|---|---|---|---|
| H | H | H | H | 0 | $CH_3$ | H | CH |
| H | H | H | H | 0 | $OCH_3$ | H | CH |
| H | H | H | H | 0 | $OCH_3$ | $\underline{n}$-$C_4H_9$ | N |
| H | H | H | H | 0 | $OCH_3$ | $CH_3$ | N |
| H | H | H | H | 0 | $OCH_3$ | $C_2H_5$ | CH |
| H | H | H | H | 0 | $OCH_3$ | $\underline{n}$-$C_3H_7$ | CH |
| H | H | $CH_3$ | H | 0 | $CH_3$ | H | CH |
| H | $CH_3$ | H | H | 0 | $OCH_3$ | H | N |
| H | H | H | H | 1 | $OCH_3$ | H | CH |
| H | H | H | H | 0 | $OCH_3$ | H | N |
| $CH_3$ | H | H | H | 0 | $CH_3$ | H | N |
| $CH_3$ | H | H | H | 0 | $OCH_2CH_3$ | H | N |
| $CH_3$ | H | H | H | 0 | $OCH_3$ | H | CH |
| $CH_3$ | H | H | H | 0 | $CH_3$ | H | CH |
| $C_2H_5$ | H | H | H | 0 | $OCH_3$ | H | N |
| $C_2H_5$ | H | H | H | 0 | $CH_3$ | H | CH |
| $C_2H_5$ | H | H | H | 0 | $OCH_3$ | H | CH |
| $CH(CH_3)_2$ | H | H | H | 0 | $CH_3$ | H | CH |
| $(CH_2)_3CH_3$ | H | H | H | 0 | $OCH_3$ | H | CH |
| $(CH_2)_2CH(CH_3)_2$ | H | H | H | 0 | $OCH_3$ | H | CH |
| $CH_2CF_3$ | H | H | H | 0 | $OCH_3$ | H | N |
| $(CH_2)_3Cl$ | H | H | H | 0 | $OCH_3$ | H | CH |
| $CH_2CH_2OCH_3$ | H | H | H | 0 | $OCH_3$ | H | CH |
| $(CH_2)_2CH(OCH_3)CH_3$ | H | H | H | 0 | $OCH_3$ | H | CH |
| $CH_2CH=CH_2$ | H | H | H | 0 | $OCH_3$ | H | CH |
| $CH_2C(CH_3)=CH_2$ | H | H | H | 0 | $OCH_3$ | H | CH |
| $CH_2C_6H_5$ | H | H | H | 0 | $OCH_3$ | H | CH |
| $CH_2C\equiv CH$ | H | H | H | 0 | $OCH_3$ | H | CH |
| $CH_2C\equiv CCH_3$ | H | H | H | 0 | $OCH_3$ | H | CH |
| $CH_3$ | H | H | H | 0 | $OCH_3$ | $(CH_2)_4CH_3$ | CH |
| $CH_2CH_2F$ | H | H | H | 0 | $OCH_3$ | H | CH |
| $CH_2CH_2F$ | H | H | H | 0 | $OCH_3$ | H | N |
| $CH_2CH_2Cl$ | H | H | H | 0 | $CH_3$ | H | CH |
| $CH_2CH_2Cl$ | H | H | H | 0 | $OCH_3$ | H | CH |
| $CH_2CH_2Cl$ | H | H | 7-Cl | 0 | $CH_3$ | H | CH |
| $CH_2CH_2Cl$ | H | H | 6-Cl | 0 | $OCH_3$ | H | CH |
| $CH_2CH_2OCH_3$ | H | H | H | 0 | $OCH_3$ | H | N |
| $CH_2CH_2OCH_3$ | H | H | 7-Cl | 0 | $CH_3$ | H | CH |
| $CH_2CH_2OCH_3$ | H | H | 6-$CH_3$ | 0 | $OCH_3$ | H | CH |
| $CH_3$ | H | H | 6-Cl | 1 | $OCH_3$ | H | CH |
| $CH_3$ | H | H | 6-$OCH_3$ | 0 | $OCH_3$ | H | CH |
| $CH_3$ | H | H | 6-$CH_3$ | 0 | $OCH_3$ | H | CH |
| $CH_3$ | H | H | 6-$OCF_2H$ | 0 | $OCH_3$ | H | CH |
| $CH_3$ | H | H | 6-Cl | 0 | $OCH_3$ | H | CH |
| $CH_3$ | H | H | 6-$CF_3$ | 0 | $OCH_3$ | H | CH |
| $CH_3$ | H | H | 6-$SCH_3$ | 0 | $OCH_3$ | H | CH |
| $CH_3$ | H | H | 6-Br | 0 | $OCH_3$ | H | CH |
| $CH_3$ | H | H | 6-F | 0 | $OCH_3$ | H | CH |
| $CF_2H$ | H | H | H | 0 | $OCH_3$ | H | CH |
| $CF_2H$ | H | H | H | 0 | $OCH_3$ | H | N |
| $CF_2H$ | H | H | H | 0 | $CH_3$ | H | CH |
| $CF_2H$ | H | H | 6-Cl | 0 | $OCH_3$ | H | CH |
| $CH_2CH_2OCH_2CH_3$ | H | H | H | 0 | $OCH_3$ | H | CH |

TABLE X-continued

General Structure X

| $R_{12}$ | $R_9$ | R | $R_2$ | m | X | Y | Z |
|---|---|---|---|---|---|---|---|
| CH₂CH₂OCH₂CH₃ | H | H | H | 0 | OCH₃ | H | N |
| CH₂CH₂OCH₂CH₃ | H | H | H | 0 | CH₃ | H | CH |
| CH₂CH₂OCH₂CH₃ | H | H | 7-Cl | 0 | OCH₃ | H | CH |
| CH₂CH₂OCH₂CH₃ | H | H | 6-Cl | 0 | OCH₃ | H | CH |
| CH₂CH=CH₂ | H | H | H | 0 | OCH₃ | H | N |
| CH₂CH=CH₂ | H | H | H | 0 | CH₃ | H | CH |
| CH₂CH=CH₂ | H | H | H | 0 | CH₃ | H | N |
| CH₂CH=CH₂ | H | H | 7-Cl | 0 | OCH₃ | H | CH |
| CH₂CH=CH₂ | H | H | 6-OCH₃ | 0 | OCH₃ | H | CH |

TABLE XI

General Structure XI

| L | $R_{13}$ | $R_{14}$ | $R_2$ | R | X | Y | Z |
|---|---|---|---|---|---|---|---|
| L-15 | H | — | H | H | CH₃ | H | CH |
| L-15 | H | — | H | H | OCH₃ | H | CH |
| L-15 | H | — | H | H | OCH₃ | H | N |
| L-15 | CH₃ | — | H | H | CH₃ | H | CH |
| L-15 | CH₃ | — | H | H | OCH₃ | H | CH |
| L-15 | CH₃ | — | H | H | OCH₃ | H | N |
| L-15 | C₂H₅ | — | H | H | CH₃ | H | CH |
| L-15 | C₂H₅ | — | H | H | OCH₃ | H | N |
| L-15 | n-C₃H₇ | — | H | H | OCH₃ | H | N |
| L-16 | H | — | H | H | CH₃ | H | CH |
| L-16 | H | — | H | H | OCH₃ | H | N |
| L-16 | H | — | H | H | OCH₃ | H | CH |
| L-16 | CH₃ | — | H | H | OCH₃ | H | N |
| L-16 | CH₃ | — | H | H | OCH₃ | H | CH |
| L-16 | CH₃ | — | H | H | CH₃ | H | CH |
| L-17 | CH₃ | H | H | H | CH₃ | H | CH |
| L-17 | CH₃ | H | H | H | OCH₃ | H | N |
| L-17 | CH₃ | H | H | H | OCH₃ | H | CH |
| L-17 | CH₃ | H | H | H | CH₃ | H | N |
| L-17 | CH₃ | H | H | H | OCH₃ | CH₃ | CH |
| L-17 | CH₃ | H | H | H | OCH₃ | C₂H₅ | CH |
| L-17 | CH₃ | H | H | H | OCH₃ | n-C₃H₇ | CH |
| L-17 | CH₃ | CH₃ | H | H | OCH₃ | H | N |
| L-17 | CH₃ | CH₃ | H | H | OCH₃ | H | CH |
| L-17 | CH₃ | CH₃ | H | H | CH₃ | H | CH |
| L-17 | C₂H₅ | H | H | H | OCH₃ | H | N |
| L-17 | C₂H₅ | H | H | H | OCH₃ | H | CH |
| L-17 | C₂H₅ | H | H | H | CH₃ | H | CH |
| L-17 | (CH₂)₂CH₃ | H | H | H | OCH₃ | H | CH |
| L-17 | CH₃ | H | H | CH₃ | OCH₃ | H | N |
| L-17 | CH₃ | H | H | H | OCH₂CH₃ | H | CH |
| L-17 | CH₃ | H | 6-Cl | H | OCH₃ | H | CH |
| L-17 | CH₃ | H | 6-CF₃ | H | OCH₃ | H | CH |
| L-17 | CH₃ | H | 6-Br | H | OCH₃ | H | CH |
| L-17 | CH₃ | H | 6-F | H | OCH₃ | H | CH |
| L-17 | CH₃ | H | 6-CH₃ | H | OCH₃ | H | CH |
| L-17 | CH₃ | H | 6-OCH₃ | H | OCH₃ | H | CH |
| L-17 | CH₃ | H | 6-OCF₂H | H | OCH₃ | H | CH |
| L-17 | CH₃ | H | 6-SCH₃ | H | OCH₃ | H | CH |
| L-17 | CH₃ | H | 7-Cl | H | OCH₃ | H | CH |
| L-17 | CH₃ | H | 6-Cl | H | OCH₃ | H | N |
| L-17 | CH₃ | H | H | H | OCH₃ | (CH₂)₃CH₃ | CH |

TABLE XII

General Structure XII

| $R_{13}$ | $R_{15}$ | R | X | Y | Z |
|---|---|---|---|---|---|
| H | Cl | H | CH₃ | H | CH |
| CH₃ | Cl | H | CH₃ | H | CH |
| CH₃ | Cl | H | OCH₃ | H | N |
| CH₃ | Cl | H | OCH₃ | H | CH |
| CH₃ | CH₃ | H | CH₃ | H | CH |
| CH₃ | CH₃ | H | OCH₃ | H | CH |
| CH₃ | CH₃ | H | OCH₃ | H | N |
| CH₃ | F | H | OCH₃ | H | CH |
| CH₃ | Br | H | CH₃ | H | CH |
| CH₃ | Br | H | OCH₃ | H | N |
| CH₃ | Br | H | OCH₃ | H | CH |
| CH₃ | NO₂ | H | CH₃ | H | CH |
| CH₃ | NO₂ | H | OCH₃ | H | N |
| CH₃ | NO₂ | H | OCH₃ | H | CH |
| CH₃ | CO₂CH₃ | H | OCH₃ | H | N |
| CH₃ | CO₂CH₃ | H | CH₃ | H | N |
| CH₃ | CO₂CH₃ | H | CH₃ | H | CH |
| CH₃ | CO₂CH₃ | H | OCH₃ | H | CH |
| CH₃ | CO₂C₂H₅ | H | CH₃ | H | CH |
| CH₃ | CO₂C₂H₅ | H | OCH₃ | H | CH |
| CH₃ | CO₂C₂H₅ | H | OCH₃ | H | N |
| CH₃ | SO₂N(CH₃)₂ | H | CH₃ | H | CH |
| CH₃ | SO₂N(CH₃)₂ | H | OCH₃ | H | N |
| CH₃ | SO₂N(CH₃)₂ | H | OCH₃ | H | CH |
| CH₃ | SO₂CH₃ | H | CH₃ | H | CH |
| CH₃ | SO₂CH₃ | H | OCH₃ | H | CH |
| CH₃ | SO₂CH₃ | H | OCH₃ | H | N |
| CH₃ | SO₂C₂H₅ | H | CH₃ | H | CH |
| CH₃ | SO₂C₂H₅ | H | OCH₃ | H | N |
| CH₃ | SO₂C₂H₅ | H | OCH₃ | H | CH |

TABLE XII-continued

General Structure XII

| R13 | R15 | R | X | Y | Z |
|---|---|---|---|---|---|
| CH3 | SO2(CH2)2CH3 | H | CH3 | H | CH |
| CH3 | SO2(CH2)2CH3 | H | OCH3 | H | CH |
| CH3 | SO2(CH2)2CH3 | H | OCH3 | H | N |
| CH3 | SO2CH2CH=CH2 | H | CH3 | H | CH |
| CH3 | SO2CH2CH=CH2 | H | OCH3 | H | N |
| CH3 | SO2CH2CH=CH2 | H | OCH3 | H | CH |
| C2H5 | CO2CH3 | H | OCH3 | H | CH |
| (CH2)2CH3 | CO2CH3 | H | OCH3 | H | CH |
| CH3 | CO2CH3 | CH3 | OCH3 | H | CH |
| CH3 | CO2CH3 | H | OCH3 | (CH2)4CH3 | CH |
| CH3 | CO2CH3 | H | OCH3 | (CH2)3CH3 | N |
| CH3 | CH2CH2CH3 | H | OCH3 | H | CH |
| CH3 | OCF2H | H | OCH3 | H | CH |
| CH3 | OCF2H | H | OCH3 | H | N |

TABLE XIIA

General Structure XIIA

| R13 | R15 | R | X | Y | Z |
|---|---|---|---|---|---|
| H | Cl | H | CH3 | H | CH |
| CH3 | Cl | H | CH3 | H | CH |
| CH3 | Cl | H | OCH3 | H | N |
| CH3 | Cl | H | OCH3 | H | CH |
| CH3 | CH3 | H | CH3 | H | CH |
| CH3 | CH3 | H | OCH3 | H | CH |
| CH3 | CH3 | H | OCH3 | H | N |
| CH3 | F | H | OCH3 | H | CH |
| CH3 | Br | H | CH3 | H | CH |
| CH3 | Br | H | OCH3 | H | N |
| CH3 | Br | H | OCH3 | H | CH |
| CH3 | NO2 | H | CH3 | H | CH |
| CH3 | NO2 | H | OCH3 | H | N |
| CH3 | NO2 | H | OCH3 | H | CH |
| CH3 | CO2CH3 | H | OCH3 | H | N |
| CH3 | CO2CH3 | H | CH3 | H | N |
| CH3 | CO2CH3 | H | CH3 | H | CH |
| CH3 | CO2CH3 | H | OCH3 | H | CH |
| CH3 | CO2C2H5 | H | CH3 | H | CH |
| CH3 | CO2C2H5 | H | OCH3 | H | CH |
| CH3 | CO2C2H5 | H | OCH3 | H | N |
| CH3 | SO2N(CH3)2 | H | CH3 | H | CH |
| CH3 | SO2N(CH3)2 | H | OCH3 | H | N |
| CH3 | SO2N(CH3)2 | H | OCH3 | H | CH |
| CH3 | SO2CH3 | H | CH3 | H | CH |
| CH3 | SO2CH3 | H | OCH3 | H | CH |
| CH3 | SO2CH3 | H | OCH3 | H | N |
| CH3 | SO2C2H5 | H | CH3 | H | CH |
| CH3 | SO2C2H5 | H | OCH3 | H | N |
| CH3 | SO2C2H5 | H | OCH3 | H | CH |
| CH3 | SO2(CH2)2CH3 | H | CH3 | H | CH |
| CH3 | SO2(CH2)2CH3 | H | OCH3 | H | CH |
| CH3 | SO2(CH2)2CH3 | H | OCH3 | H | N |
| CH3 | SO2CH2CH=CH2 | H | CH3 | H | CH |
| CH3 | SO2CH2CH=CH2 | H | OCH3 | H | N |
| CH3 | SO2CH2CH=CH2 | H | OCH3 | H | CH |
| C2H5 | CO2CH3 | H | OCH3 | H | CH |
| (CH2)2CH3 | CO2CH3 | H | OCH3 | H | CH |
| CH3 | CO2CH3 | CH3 | OCH3 | H | CH |
| CH3 | CO2CH3 | H | OCH3 | (CH2)3CH3 | N |
| CH3 | CO2CH3 | H | OCH3 | (CH2)4CH3 | CH |
| CH3 | SO2N(CH3)2 | H | OCH3 | (CH2)3CH3 | CH |
| CH3 | CH2CH3 | H | OCH3 | H | CH |
| CH3 | OCF2H | H | OCH3 | H | CH |
| CH3 | OCF2H | H | OCH3 | H | N |

TABLE XIIB

General Structure XIIB

| R13 | R15 | R | X | Y | Z |
|---|---|---|---|---|---|
| H | Cl | H | CH3 | H | CH |
| CH3 | Cl | H | CH3 | H | CH |
| CH3 | Cl | H | OCH3 | H | N |
| CH3 | Cl | H | OCH3 | H | CH |
| CH3 | CH3 | H | CH3 | H | CH |
| CH3 | CH3 | H | OCH3 | H | CH |
| CH3 | CH3 | H | OCH3 | H | N |
| CH3 | F | H | OCH3 | H | CH |
| CH3 | Br | H | CH3 | H | CH |
| CH3 | Br | H | OCH3 | H | N |
| CH3 | Br | H | OCH3 | H | CH |
| CH3 | NO2 | H | CH3 | H | CH |
| CH3 | NO2 | H | OCH3 | H | N |
| CH3 | NO2 | H | OCH3 | H | CH |
| CH3 | CO2CH3 | H | OCH3 | H | N |
| CH3 | CO2CH3 | H | CH3 | H | N |
| CH3 | CO2CH3 | H | CH3 | H | CH |
| CH3 | CO2CH3 | H | OCH3 | H | CH |
| CH3 | CO2C2H5 | H | CH3 | H | CH |
| CH3 | CO2C2H5 | H | OCH3 | H | CH |
| CH3 | CO2C2H5 | H | OCH3 | H | N |
| CH3 | SO2N(CH3)2 | H | CH3 | H | CH |
| CH3 | SO2N(CH3)2 | H | OCH3 | H | N |
| CH3 | SO2N(CH3)2 | H | OCH3 | H | CH |
| CH3 | SO2CH3 | H | CH3 | H | CH |
| CH3 | SO2CH3 | H | OCH3 | H | CH |
| CH3 | SO2CH3 | H | OCH3 | H | N |
| CH3 | SO2C2H5 | H | CH3 | H | CH |
| CH3 | SO2C2H5 | H | OCH3 | H | N |
| CH3 | SO2C2H5 | H | OCH3 | H | CH |
| CH3 | SO2(CH2)2CH3 | H | CH3 | H | CH |
| CH3 | SO2(CH2)2CH3 | H | OCH3 | H | CH |
| CH3 | SO2(CH2)2CH3 | H | OCH3 | H | N |
| CH3 | SO2CH2CH=CH2 | H | CH3 | H | CH |
| CH3 | SO2CH2CH=CH2 | H | OCH3 | H | N |
| CH3 | SO2CH2CH=CH2 | H | OCH3 | H | CH |
| C2H5 | CO2CH3 | H | OCH3 | H | CH |
| (CH2)2CH3 | CO2CH3 | H | OCH3 | H | CH |
| CH3 | CO2CH3 | CH3 | OCH3 | H | CH |
| CH3 | CO2CH3 | H | OCH3 | (CH2)4CH3 | CH |

TABLE XIII

General Structure XIII

| L | R13 | R16 | R | X | Y | Z |
|---|---|---|---|---|---|---|
| L-19 | H | — | H | CH3 | H | CH |
| L-19 | H | — | H | OCH3 | H | N |
| L-19 | H | — | H | OCH3 | H | CH |
| L-19 | CH3 | — | H | CH3 | H | CH |
| L-19 | CH3 | — | H | OCH3 | H | CH |
| L-19 | CH3 | — | H | OCH3 | H | N |
| L-19 | C2H5 | — | H | OCH3 | H | CH |
| L-19 | (CH2)2CH3 | — | H | OCH3 | H | CH |
| L-20 | H | H | H | OCH3 | H | CH |
| L-20 | H | CO2CH3 | H | OCH3 | H | N |
| L-20 | H | CO2CH3 | H | CH3 | H | N |
| L-20 | H | CO2CH3 | H | OCH3 | H | CH |
| L-20 | H | CO2CH3 | H | CH3 | H | CH |
| L-20 | H | CO2C2H5 | H | OCH3 | H | CH |
| L-20 | H | CO2C2H5 | H | OCH3 | H | N |
| L-20 | H | CO2C2H5 | H | CH3 | H | CH |
| L-20 | H | SO2CH3 | H | CH3 | H | CH |
| L-20 | H | SO2CH3 | H | OCH3 | H | N |
| L-20 | H | SO2CH3 | H | OCH3 | H | CH |
| L-20 | H | SO2C2H5 | H | CH3 | H | CH |
| L-20 | H | SO2C2H5 | H | OCH3 | H | N |
| L-20 | H | SO2C2H5 | H | OCH3 | H | CH |
| L-20 | H | CO2CH3 | H | OCH3 | (CH2)3CH3 | CH |

TABLE XIV

General Structure XIV

| L | R1 | R2 | R3 | R4 | R5 | R6 | X1 | Y1 |
|---|---|---|---|---|---|---|---|---|
| L-1 | CO2CH3 | H | — | — | — | — | H | O |
| L-1 | CO2CH3 | H | — | — | — | — | CH3 | O |
| L-1 | CO2C2H5 | H | — | — | — | — | H | O |

TABLE XIV-continued

General Structure XIV

| L | $R_1$ | $R_2$ | $R_3$ | $R_4$ | $R_5$ | $R_6$ | $X_1$ | $Y_1$ |
|---|---|---|---|---|---|---|---|---|
| L-1 | $SO_2N(CH_3)_2$ | H | — | — | — | — | H | O |
| L-1 | $SO_2N(CH_3)_2$ | H | — | — | — | — | $CH_3$ | O |
| L-1 | $OSO_2CH_3$ | H | — | — | — | — | H | O |
| L-1 | $OSO_2CH_3$ | H | — | — | — | — | $CH_3$ | O |
| L-1 | $OCF_2H$ | H | — | — | — | — | H | O |
| L-1 | $OCF_2H$ | H | — | — | — | — | $CH_3$ | O |
| L-1 | $OCH_2CH=CH_2$ | H | — | — | — | — | H | O |
| L-1 | Q-1 | H | — | — | — | — | H | O |
| L-1 | $CO_2CH_3$ | H | — | — | — | — | H | $CH_2$ |
| L-1 | $CO_2Et$ | H | — | — | — | — | H | $CH_2$ |
| L-1 | $SO_2N(CH_3)_2$ | H | — | — | — | — | H | $CH_2$ |
| L-1 | $OSO_2CH_3$ | H | — | — | — | — | H | $CH_2$ |
| L-1 | $OCF_2H$ | H | — | — | — | — | H | $CH_2$ |
| L-2 | — | — | Cl | — | — | — | H | O |
| L-2 | — | — | $CH_3$ | — | — | — | H | O |
| L-2 | — | — | $OCH_3$ | — | — | — | H | O |
| L-2 | — | — | $SO_2CH_3$ | — | — | — | H | O |
| L-2 | — | — | $OSO_2CH_3$ | — | — | — | H | O |
| L-2 | — | — | Cl | — | — | — | H | $CH_2$ |
| L-2 | — | — | $SO_2CH_3$ | — | — | — | H | $CH_2$ |
| L-2 | — | — | $OCH_3$ | — | — | — | H | $CH_2$ |
| L-2 | — | — | $OSO_2CH_3$ | — | — | — | H | $CH_2$ |
| L-3 | — | — | — | Cl | — | — | H | O |
| L-3 | — | — | — | $CH_3$ | — | — | H | O |
| L-3 | — | — | — | $OCH_3$ | — | — | H | O |
| L-3 | — | — | — | $SO_2N(CH_3)_2$ | — | — | H | O |
| L-3 | — | — | — | $SO_2CH_3$ | — | — | H | O |
| L-3 | — | — | — | $OCH_2CH=CH_2$ | — | — | H | O |
| L-3 | — | — | — | $CH_2OCH_3$ | — | — | H | O |
| L-3 | — | — | — | Cl | — | — | H | $CH_2$ |
| L-3 | — | — | — | $OCH_3$ | — | — | H | $CH_2$ |
| L-3 | — | — | — | $SO_2N(CH_3)_2$ | — | — | H | $CH_2$ |
| L-3 | — | — | — | $SO_2CH_3$ | — | — | H | $CH_2$ |
| L-4 | — | — | — | — | $CO_2CH_3$ | — | H | O |
| L-4 | — | — | — | — | $CO_2C_2H_5$ | — | H | O |
| L-4 | — | — | — | — | $NO_2$ | — | H | O |
| L-4 | — | — | — | — | Cl | — | H | O |
| L-4 | — | — | — | — | $CH_3$ | — | H | O |
| L-4 | — | — | — | — | $SO_2N(CH_3)_2$ | — | H | O |
| L-4 | — | — | — | — | $SO_2CH_3$ | — | H | O |
| L-4 | — | — | — | — | $CO_2CH_3$ | — | H | $CH_2$ |
| L-4 | — | — | — | — | $CO_2C_2H_5$ | — | H | $CH_2$ |
| L-4 | — | — | — | — | $SO_2CH_3$ | — | H | $CH_2$ |
| L-4 | — | — | — | — | $SO_2N(CH_3)_2$ | — | H | $CH_2$ |
| L-4 | — | — | — | — | $NO_2$ | — | H | $CH_2$ |
| L-4 | — | — | — | — | Cl | — | H | $CH_2$ |
| L-5 | — | — | — | — | $CO_2CH_3$ | — | H | O |
| L-5 | — | — | — | — | $CO_2C_2H_5$ | — | H | O |
| L-5 | — | — | — | — | $SO_2CH_3$ | — | H | O |
| L-5 | — | — | — | — | $SO_2N(CH_3)_2$ | — | H | O |
| L-5 | — | — | — | — | $NO_2$ | — | H | O |
| L-5 | — | — | — | — | Cl | — | H | O |
| L-5 | — | — | — | — | $SO_2CH_3$ | — | H | $CH_2$ |
| L-5 | — | — | — | — | $CO_2CH_3$ | — | H | $CH_2$ |
| L-5 | — | — | — | — | $SO_2N(CH_3)_2$ | — | H | $CH_2$ |
| L-5 | — | — | — | — | $NO_2$ | — | H | $CH_2$ |
| L-6 | — | — | — | — | $CO_2CH_3$ | — | H | O |
| L-6 | — | — | — | — | Br | — | H | O |
| L-6 | — | — | — | — | $SO_2CH_3$ | — | H | O |
| L-6 | — | — | — | — | $SO_2N(CH_3)_2$ | — | H | O |
| L-6 | — | — | — | — | $CO_2CH_3$ | — | H | $CH_2$ |
| L-6 | — | — | — | — | Br | — | H | $CH_2$ |
| L-7 | — | — | — | — | — | $CO_2CH_3$ | H | O |
| L-7 | — | — | — | — | — | $CO_2C_2H_5$ | H | O |
| L-7 | — | — | — | — | — | $SO_2CH_3$ | H | O |
| L-7 | — | — | — | — | — | $SO_2N(CH_3)_2$ | H | O |
| L-7 | — | — | — | — | — | $OCH_3$ | H | O |
| L-7 | — | — | — | — | — | $OSO_2CH_3$ | H | O |
| L-7 | — | — | — | — | — | $CO_2CH_3$ | H | $CH_2$ |
| L-7 | — | — | — | — | — | $SO_2CH_3$ | H | $CH_2$ |
| L-7 | — | — | — | — | — | $SO_2N(CH_3)_2$ | H | $CH_2$ |
| L-7 | — | — | — | — | — | $OCH_3$ | H | $CH_2$ |
| L-7 | — | — | — | — | — | $CO_2CH_3$ | $CH_3$ | O |

TABLE XV

General Structure XV

| L | $R_1$ | $R_2$ | $R_3$ | $R_4$ | $R_5$ | $R_6$ | $X_1$ |
|---|---|---|---|---|---|---|---|
| L-1 | $CO_2CH_3$ | H | — | — | — | — | H |
| L-1 | $CO_2CH_3$ | H | — | — | — | — | $CH_3$ |
| L-1 | $CO_2C_2H_5$ | H | — | — | — | — | H |
| L-1 | $SO_2N(CH_3)_2$ | H | — | — | — | — | H |
| L-1 | $SO_2N(CH_3)_2$ | H | — | — | — | — | $CH_3$ |
| L-1 | $OSO_2CH_3$ | H | — | — | — | — | H |
| L-1 | $OSO_2CH_3$ | H | — | — | — | — | $CH_3$ |
| L-1 | $OCF_2H$ | H | — | — | — | — | H |
| L-1 | $OCF_2H$ | H | — | — | — | — | $CH_3$ |
| L-1 | $OCH_2CH=CH_2$ | H | — | — | — | — | H |
| L-1 | Q-1 | H | — | — | — | — | H |
| L-2 | — | — | Cl | — | — | — | H |
| L-2 | — | — | $CH_3$ | — | — | — | H |
| L-2 | — | — | $OCH_3$ | — | — | — | H |
| L-2 | — | — | $SO_2CH_3$ | — | — | — | H |
| L-2 | — | — | $OSO_2CH_3$ | — | — | — | H |
| L-3 | — | — | — | Cl | — | — | H |
| L-3 | — | — | — | $CH_3$ | — | — | H |
| L-3 | — | — | — | $OCH_3$ | — | — | H |
| L-3 | — | — | — | $SO_2N(CH_3)_2$ | — | — | H |
| L-3 | — | — | — | $SO_2CH_3$ | — | — | H |
| L-3 | — | — | — | $OCH_2CH=CH_2$ | — | — | H |
| L-3 | — | — | — | $CH_2OCH_3$ | — | — | H |
| L-4 | — | — | — | — | $CO_2CH_3$ | — | H |
| L-4 | — | — | — | — | $CO_2C_2H_5$ | — | H |
| L-4 | — | — | — | — | $NO_2$ | — | H |
| L-4 | — | — | — | — | Cl | — | H |
| L-4 | — | — | — | — | $CH_3$ | — | H |
| L-4 | — | — | — | — | $SO_2N(CH_3)_2$ | — | H |
| L-4 | — | — | — | — | $SO_2CH_3$ | — | H |
| L-4 | — | — | — | — | Cl | — | H |
| L-5 | — | — | — | — | $CO_2CH_3$ | — | H |
| L-5 | — | — | — | — | $CO_2C_2H_5$ | — | H |
| L-5 | — | — | — | — | $SO_2CH_3$ | — | H |
| L-5 | — | — | — | — | $SO_2N(CH_3)_2$ | — | H |
| L-5 | — | — | — | — | $NO_2$ | — | H |
| L-5 | — | — | — | — | Cl | — | H |
| L-6 | — | — | — | — | $CO_2CH_3$ | — | H |
| L-6 | — | — | — | — | Br | — | H |
| L-6 | — | — | — | — | $SO_2CH_3$ | — | H |
| L-6 | — | — | — | — | $SO_2N(CH_3)_2$ | — | H |
| L-7 | — | — | — | — | — | $CO_2CH_3$ | H |
| L-7 | — | — | — | — | — | $CO_2C_2H_5$ | H |
| L-7 | — | — | — | — | — | $SO_2CH_3$ | H |
| L-7 | — | — | — | — | — | $SO_2N(CH_3)_2$ | H |
| L-7 | — | — | — | — | — | $OCH_3$ | H |
| L-7 | — | — | — | — | — | $OSO_3CH_3$ | H |

TABLE XVI

General Structure XVI

| L | $R_1$ | $R_2$ | $R_3$ | $R_4$ | $R_5$ | $R_6$ | $X_1$ | $Y_2$ |
|---|---|---|---|---|---|---|---|---|
| L-1 | $CO_2CH_3$ | H | — | — | — | — | H | H |
| L-1 | $CO_2CH_3$ | H | — | — | — | — | $CH_3$ | H |
| L-1 | $CO_2C_2H_5$ | H | — | — | — | — | H | H |
| L-1 | $SO_2N(CH_3)_2$ | H | — | — | — | — | H | H |
| L-1 | $SO_2N(CH_3)_2$ | H | — | — | — | — | $CH_3$ | H |
| L-1 | $OSO_2CH_3$ | H | — | — | — | — | H | H |
| L-1 | $OSO_2CH_3$ | H | — | — | — | — | $CH_3$ | H |
| L-1 | $OCF_2H$ | H | — | — | — | — | H | H |
| L-1 | $OCF_2H$ | H | — | — | — | — | $CH_3$ | H |
| L-1 | $OCH_2CH=CH_2$ | H | — | — | — | — | H | H |
| L-1 | Q-1 | H | — | — | — | — | H | H |
| L-1 | $CO_2CH_3$ | H | — | — | — | — | H | $CH_3$ |
| L-1 | $CO_2Et$ | H | — | — | — | — | H | $CH_3$ |
| L-1 | $SO_2N(CH_3)_2$ | H | — | — | — | — | H | $CH_3$ |
| L-1 | $OSO_2CH_3$ | H | — | — | — | — | H | $CH_3$ |
| L-1 | $OCF_2H$ | H | — | — | — | — | H | $CH_3$ |
| L-2 | — | — | Cl | — | — | — | H | H |
| L-2 | — | — | $CH_3$ | — | — | — | H | H |
| L-2 | — | — | $OCH_3$ | — | — | — | H | H |
| L-2 | — | — | $SO_2CH_3$ | — | — | — | H | H |
| L-2 | — | — | $OSO_2CH_3$ | — | — | — | H | H |
| L-2 | — | — | Cl | — | — | — | H | $CH_3$ |
| L-2 | — | — | $SO_2CH_3$ | — | — | — | H | $CH_3$ |
| L-2 | — | — | $OCH_3$ | — | — | — | H | $CH_3$ |
| L-2 | — | — | $OSO_2CH_3$ | — | — | — | H | $CH_3$ |
| L-3 | — | — | — | Cl | — | — | H | H |

TABLE XVI-continued

General Structure XVI

| L | R₁ | R₂ | R₃ | R₄ | R₅ | R₆ | X₁ | Y₂ |
|---|---|---|---|---|---|---|---|---|
| L-3 | — | — | — | CH₃ | — | — | H | H |
| L-3 | — | — | — | OCH₃ | — | — | H | H |
| L-3 | — | — | — | SO₂N(CH₃)₂ | — | — | H | H |
| L-3 | — | — | — | SO₂CH₃ | — | — | H | H |
| L-3 | — | — | — | OCH₂CH=CH₂ | — | — | H | H |
| L-3 | — | — | — | CH₂OCH₃ | — | — | H | H |
| L-3 | — | — | — | Cl | — | — | H | CH₃ |
| L-3 | — | — | — | OCH₃ | — | — | H | CH₃ |
| L-3 | — | — | — | SO₂N(CH₃)₂ | — | — | H | CH₃ |
| L-3 | — | — | — | SO₂CH₃ | — | — | H | CH₃ |
| L-4 | — | — | — | — | CO₂CH₃ | — | H | H |
| L-4 | — | — | — | — | CO₂C₂H₅ | — | H | H |
| L-4 | — | — | — | — | NO₂ | — | H | H |
| L-4 | — | — | — | — | Cl | — | H | H |
| L-4 | — | — | — | — | CH₃ | — | H | H |
| L-4 | — | — | — | — | SO₂N(CH₃)₂ | — | H | H |
| L-4 | — | — | — | — | SO₂CH₃ | — | H | H |
| L-4 | — | — | — | — | CO₂CH₃ | — | H | CH₃ |
| L-4 | — | — | — | — | CO₂C₂H₅ | — | H | CH₃ |
| L-4 | — | — | — | — | SO₂CH₃ | — | H | CH₃ |
| L-4 | — | — | — | — | SO₂N(CH₃)₂ | — | H | CH₃ |
| L-4 | — | — | — | — | NO₂ | — | H | CH₃ |
| L-4 | — | — | — | — | Cl | — | H | CH₃ |
| L-5 | — | — | — | — | CO₂CH₃ | — | H | H |
| L-5 | — | — | — | — | CO₂C₂H₅ | — | H | H |
| L-5 | — | — | — | — | SO₂CH₃ | — | H | H |
| L-5 | — | — | — | — | SO₂N(CH₃)₂ | — | H | H |
| L-5 | — | — | — | — | NO₂ | — | H | H |
| L-5 | — | — | — | — | Cl | — | H | H |
| L-5 | — | — | — | — | CO₂CH₃ | — | H | CH₃ |
| L-5 | — | — | — | — | SO₂CH₃ | — | H | CH₃ |
| L-5 | — | — | — | — | SO₂N(CH₃)₂ | — | H | CH₃ |
| L-5 | — | — | — | — | NO₂ | — | H | CH₃ |
| L-6 | — | — | — | — | CO₂CH₃ | — | H | H |
| L-6 | — | — | — | — | Br | — | H | H |
| L-6 | — | — | — | — | SO₂CH₃ | — | H | H |
| L-6 | — | — | — | — | SO₂N(CH₃)₂ | — | H | H |
| L-6 | — | — | — | — | CO₂CH₃ | — | H | CH₃ |
| L-6 | — | — | — | — | Br | — | H | CH₃ |
| L-7 | — | — | — | — | — | CO₂CH₃ | H | H |
| L-7 | — | — | — | — | — | CO₂C₂H₅ | H | H |
| L-7 | — | — | — | — | — | SO₂CH₃ | H | H |
| L-7 | — | — | — | — | — | SO₂N(CH₃)₂ | H | H |
| L-7 | — | — | — | — | — | OCH₃ | H | H |
| L-7 | — | — | — | — | — | OSO₃CH₃ | H | H |
| L-7 | — | — | — | — | — | CO₂CH₃ | H | CH₃ |
| L-7 | — | — | — | — | — | SO₂CH₃ | H | CH₃ |
| L-7 | — | — | — | — | — | SO₂N(CH₃)₂ | H | CH₃ |
| L-7 | — | — | — | — | — | OCH₃ | H | CH₃ |

TABLE XVII

General Structure XVII

| L | X₁ | Y₁ |
|---|---|---|
| 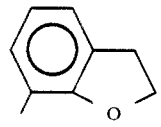 | H | O |
| 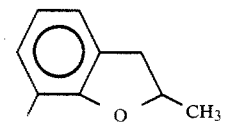 | CH₃ | O |
| 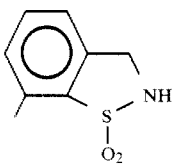 | H | CH₂ |
| 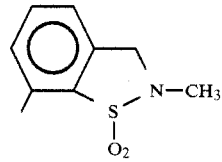 | H | O |
| 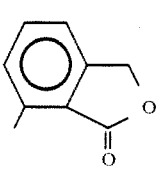 | H | O |

TABLE XVII-continued
General Structure XVII
| L | X₁ | Y₁ |
|---|---|---|
| 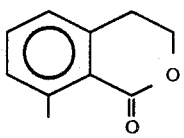 | H | O |
| 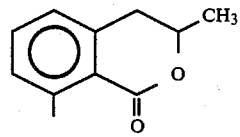 | H | O |
| 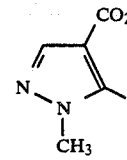 | H | O |
| 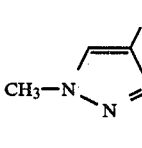 | H | O |
| 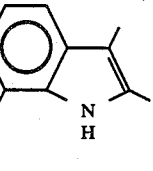 | H | O |
| 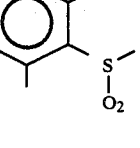 | H | O |
| 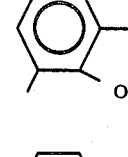 | H | O |
| 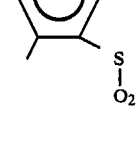 | H | O |
| 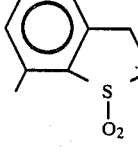 | H | O |
|  | H | O |
TABLE XVIII
General Structure XVIII
| L | X₁ |
|---|---|
| 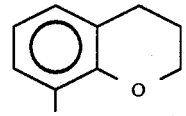 | H |
| 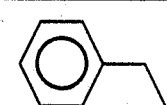 | H |
| 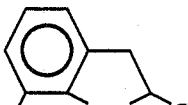 | H |
| 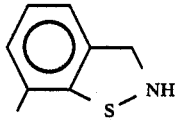 | H |
| 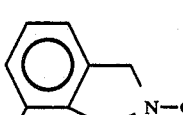 | H |
| 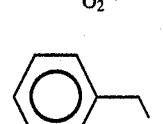 | CH₃ |
| 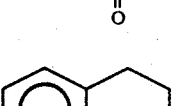 | H |
| 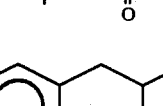 | H |

TABLE XVIII-continued

General Structure XVIII

| L | $X_1$ |
|---|---|
| (1-methyl-3-methyl-pyrazole-4-carboxylic acid methyl ester) | H |
| (methyl-indole-2-carboxylic acid ethyl ester) | H |
| (methyl-phenyl-ethyl-N-methyl sulfonamide) | H |
| (methyl-benzofuran, vinyl) | H |
| (methyl-benzothiophene-$SO_2$) | $CH_3$ |
| (methyl-phenyl-CH$_2$-CH(CH$_3$)-$SO_2$) | H |
| (methyl-chromane) | H |

TABLE XIX

General Structure XIX

| L | $X_1$ | $Y_2$ |
|---|---|---|
| (methyl-dihydrobenzofuran) | H | H |
| (methyl-phenyl-CH$_2$-CH(CH$_3$)-O) | H | H |
| (methyl-benzisothiazoline-$SO_2$, NH) | H | H |
| (methyl-benzisothiazoline-$SO_2$, N-CH$_3$) | H | $CH_3$ |
| (methyl-isobenzofuranone) | $CH_3$ | H |
| (methyl-isochromanone) | H | H |
| (methyl-phenyl-CH$_2$-CH(CH$_3$)-C(=O)-O) | H | H |
| (1-methyl-3-methyl-pyrazole-4-CO$_2$CH$_3$) | H | H |
| (1-methyl-3-methyl-pyrazole-4-CO$_2$CH$_3$ isomer) | H | H |
| (methyl-indole-2-CO$_2$C$_2$H$_5$) | H | $CH_3$ |
| (methyl-phenyl-ethyl-N-methyl sulfonamide) | H | H |

TABLE XIX-continued
General Structure XIX

| L | X₁ | Y₂ |
|---|----|----|
| [2-methylphenyl-O-CH=CH-] (benzofuran-like, open) | H | H |
| [2,3-dihydrobenzothiophene-1,1-dioxide, 7-methyl] | H | CH₃ |
| [2-methylphenyl-CH₂-CH(CH₃)-SO₂-] | H | CH₃ |
| [8-methylchroman] | H | CH₃ |

TABLE XX
General Structure XX

| L | X₁ | X₂ |
|---|----|----|
| [7-methyl-2,3-dihydrobenzofuran] | H | CH₃ |
| [8-methyl-3-methylchroman-like, O] | H | CH₃ |
| [7-methyl-2,3-dihydrobenzisothiazole-1,1-dioxide, NH] | H | CH₃ |
| [7-methyl-2,3-dihydrobenzisothiazole-1,1-dioxide, N-CH₃] | CH₃ | CH₃ |
| [7-methylisobenzofuran-1(3H)-one] | H | C₂H₅ |
| [8-methylisochroman-1-one] | H | CH₂CF₃ |
| [8-methyl-3-methylisochroman-1-one] | H | CH₃ |
| [2-methylphenyl-CO₂CH₃] | H | CH₃ |
| [2-methylphenyl-CO₂CH₃] | H | CH₂CH₃ |
| [2-methylphenyl-CO₂CH₃] | H | CH₂CF₃ |
| [2-methylphenyl-CO₂CH₂CH₃] | H | CH₃ |
| [3-methylthiophene-2-CO₂CH₃] | H | CH₃ |
| [1-methyl-2-methoxynaphthalene] | H | CH₃ |
| [1,3-dimethylpyrazole-4-CO₂CH₃] | H | CH₃ |
| [1,5-dimethylpyrazole-4-CO₂CH₃] | H | CH₃ |
| [7-methylindole with CO₂C₂H₅] | H | CH₃ |

TABLE XX-continued

General Structure XX

| L | $X_1$ | $X_2$ |
|---|---|---|
| 2-(N-methyl-methanesulfonamidomethyl)phenyl (o-tolyl-CH$_2$-S(O$_2$)-N(CH$_3$)-) | H | CH$_3$ |
| 2-(vinyloxy)phenyl | H | CH$_3$ |
| 2-(ethylsulfonyl)phenyl | H | CH$_3$ |
| 2-(1-methylethylsulfonyl)phenyl | H | CH$_3$ |
| 2-(chroman-2-yl) / 3,4-dihydro-2H-chromen-8-yl | H | CH$_3$ |
| 2-(N,N-dimethylsulfamoyl)pyridin-3-yl | H | CH$_3$ |
| 2-(methoxycarbonyl)benzyl (−CH$_2$−C$_6$H$_4$−CO$_2$CH$_3$) | H | CH$_3$ |
| 2-(3-methyl-1,2,4-oxadiazol-5-yl)phenyl (N=N, O, CH$_3$) | H | CH$_3$ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE XXI

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 4

Wettable Powder

| | |
|---|---|
| 2-[[(4-ethynyl-6-methylpyrimidin-2-yl)aminocarbonyl]-aminosulfonyl]benzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 5

Wettable Powder

| | |
|---|---|
| 2-[[(4-ethynyl-6-methylpyrimidin-2-yl)aminocarbonyl] aminosulfonyl]benzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 6

Granule

| | |
|---|---|
| Wettable Powder of Example 5 | 5% |
| attapulgite granules (U.S.S. 20–40 mesh; 0.84–0.42 mm) | 95% |

A slurry of wettable powder containing 25% solids is sprayed on the surface of attapulgite granules while tumbling in a double-cone blender. The granules are dried and packaged.

EXAMPLE 7

Extruded Pellet

| | |
|---|---|
| 2-[[(4-ethynyl-6-methylpyrimidin-2-yl)aminocarbonyl]-aminosulfonyl]benzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 8

Low Strength Granule

| | |
|---|---|
| 2-[[(4-ethynyl-6-methylpyrimidin-2-yl)aminocarbonyl]-aminosulfonyl]benzoic acid, methyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 9

Aqueous Suspension

| | |
|---|---|
| 2-[[(4-ethynyl-6-methylpyrimidin-2-yl)aminocarbonyl]-aminosulfonyl]benzoic acid, methyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 10

Solution

| | |
|---|---|
| 2-[[4-ethynyl-6-methylpyrimidin-2-yl)aminocarbonyl)-aminosulfonyl]benzoic acid, methyl ester, sodium salt | 5% |
| water | 95% |

The salt is added directly to the water with stirring to produce the solution, which may then be packaged for use.

EXAMPLE 11

Oil Suspension

| | |
|---|---|
| 2-[[(4-ethynyl-6-methylpyrimidin-2-yl)aminocarbonyl]-aminosulfonyl]benzoic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 12

Wettable Powder

| | |
|---|---|
| 2-[[(4-ethynyl-6-methylpyrimidin-2-yl)aminocarbonyl]-aminosulfonyl]benzoic acid, methyl ester | 20% |
| sodium alkylnaphthalenesulfonate | 4% |
| sodium ligninsulfonate | 4% |
| low viscosity methyl cellulose | 3% |

| | |
|---|---|
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 13

Low Strength Granule

| | |
|---|---|
| 2-[[(4-ethynyl-6-methylpyrimidin-2-yl)aminocarbonyl]-aminosulfonyl]benzoic acid, methyl ester | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 14

Granule

| | |
|---|---|
| 2-[[(4-ethynyl-6-methylpyrimidin-2-yl)aminocarbonyl]-aminosulfonyl]benzoic acid, methyl ester | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 15

High Strength Concentrate

| | |
|---|---|
| 2-[[(4-ethynyl-6-methylpyrimidin-2-yl)aminocarbonyl]-aminosulfonyl]benzoic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 16

Wettable Powder

| | |
|---|---|
| 2-[[(4-ethynyl-6-methylpyrimidin-2-yl)aminocarbonyl]-aminosulfonyl]benzoic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 17

Wettable Powder

| | |
|---|---|
| 2-[[(4-ethynyl-6-methylpyrimidin-2-yl)aminocarbonyl]-aminosulfonyl]benzoic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 18

Oil Suspension

| | |
|---|---|
| 2-[[(4-ethynyl-6-methylpyrimidin-2-yl)aminocarbonyl]-aminosulfonyl]benzoic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 19

Dust

| | |
|---|---|
| 2-[[(4-ethynyl-6-methylpyrimidin-2-yl)aminocarbonyl]-aminosulfonyl]benzoic acid, methyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.01 to 5 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

| Compounds |
|---|
| Compound 1 |
| Compound 2 |
| Compound 3 |
| Compound 4 |
| Compound 5 |
| Compound 6 |

| -continued |
|---|
| Compounds |
| Compound 7 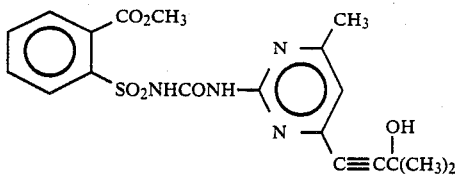 |
| Compound 8 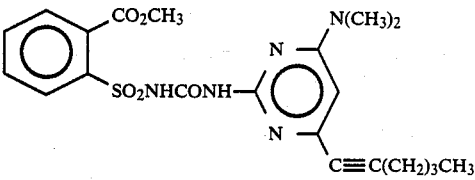 |
| Compound 9 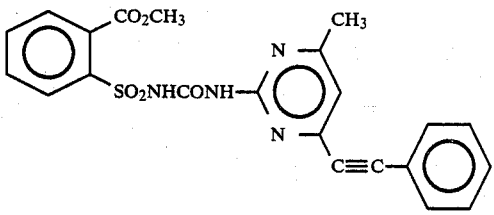 |
| Compound 10 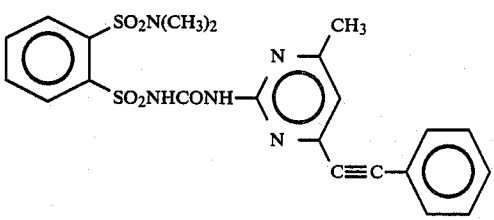 |
| Compound 11 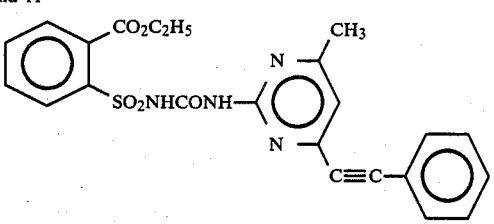 |
| Compound 12 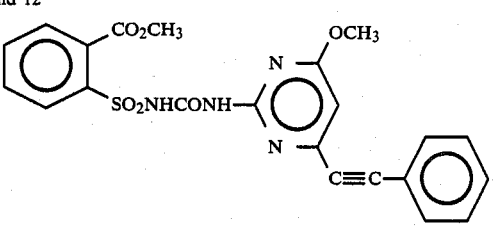 |

Test A

Seeds of crabgrass (Digitaria sp.), barnyardgrass (Echinochloa crusgalli), wild oats (Avena fatua), sicklepod (Cassia obtusifolia), morningglory (Ipomoea spp.), cocklebur (Xanthium pensylvanicum), sorghum, corn, soybean, sugarbeet, cotton, rice, wheat and purple nutsedge (Cyperus rotundus) tubers were planted and treated pre-emergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis or necrosis;
B=burn;
D=defoliation;
E=emergence inhibition;
G=growth retardation;
H=formative effects;
U=unusual pigmentation;
X=axillary stimulation;
S=albinism; and
6Y=abscised buds or flowers.

TABLE A

| Rate g/ha | Cmpd. 1 50 | Cmpd. 2 50 | Cmpd. 3 50 | Cmpd. 4 50 | Cmpd. 5 50 | Cmpd. 6 50 |
|---|---|---|---|---|---|---|
| POST-EMERGENCE | | | | | | |
| Morningglory | 4C,8H | 9C | 3C,8H | 9C | 0 | 0 |
| Cocklebur | 4C,8G | 6C,9G | 4C,9G | 6C,9G | 8G | 0 |
| Sicklepod | 9C | — | — | — | — | — |
| Nutsedge | 3C,9G | 0 | 2G | 6C,9G | 6G | 0 |
| Crabgrass | 4C,9G | 0 | 2C,8G | 0 | 5G | 0 |
| Barnyardgrass | 9C | 0 | 4C,9H | 4C,9H | 3C,9H | 0 |
| Wild Oats | 3C,9G | 0 | 2G | 4C,8G | 3G | 0 |
| Wheat | 4C,9G | 0 | 2G | 3C,8G | 3G | 0 |
| Corn | 3C,9G | 6C,9G | 9C | 9C | 3C,9H | 0 |
| Soybean | 4C,9G | 5C,9G | 4C,9G | 3H,7G | 2H,4G | 0 |
| Rice | 9C | 3C,9G | 5C,9G | 3C,8G | 5C,9G | 0 |
| Sorghum | 5C,9G | 9C | 9C | 4C,9H | 9G | 0 |
| Sugar beet | 9C | 9C | 9C | 3C,8G | 5G | 0 |
| Cotton | 9C | 3C,9G | 3C,9G | 9C | 3C,8G | 0 |
| Velvetleaf | | | | | | |
| Cheatgrass | | | | | | |
| PRE-EMERGENCE | | | | | | |
| Morningglory | 8H | 3C,9G | 8G | 9G | 5G | 0 |
| Cocklebur | 6H | 7G | 7H | 3C,8G | 8G | — |
| Sicklepod | 6G | — | — | — | — | — |
| Nutsedge | 2C,8G | 0 | 0 | 3C,5G | 0 | 0 |
| Crabgrass | 2G | 0 | 0 | 0 | 0 | 0 |
| Barnyardgrass | 9H | 0 | 4C,4H | 3C,7H | 2G | 0 |
| Wild Oats | 4C,9G | 0 | 2G | 5G | 8G | 0 |
| Wheat | 5C,9H | 0 | 0 | 2G | 6G | 2G |
| Corn | 9G | 5G | 2C,8G | 5G | 8H | 2C |
| Soybean | 2C,8G | 2C,8G | 4C,6G | 3G | 2C,5G | 0 |
| Rice | 10E | 8G | 2C,5G | 3C,8G | 4C,9H | 2C |
| Sorghum | 9H | 2C,8H | 2C,9G | 3C,7G | 3C,7G | 2C |
| Sugar beet | 3C,9G | 9C | 4C,8G | 9G | 8H | 0 |
| Cotton | 8G | 9G | 5G | 8G | 5G | 0 |
| Velvetleaf | | | | | | |
| Cheatgrass | | | | | | |

| Rate g/ha | Cmpd. 7 0.05 | Cmpd. 8 0.05 | Cmpd. 9 0.05 | Cmpd. 10 0.05 | Cmpd. 11 0.05 | Compound 12 0.4 | 0.05 |
|---|---|---|---|---|---|---|---|
| POST-EMERGENCE | | | | | | | |
| Morningglory | 2C | 2C,5G | 4G | 5G | 0 | 10C | 10C |
| Cocklebur | 2C,8G | 2C,8H | 9C | 2C,9H | 4C,9H | 9C | 10C |
| Sicklepod | 2C | — | — | — | — | — | — |
| Nutsedge | 8G | 2C,9G | 3C,8G | 0 | 2C,9G | 10C | 9C |
| Crabgrass | 2C | 0 | 2C,5G | 0 | 0 | 4C,8G | 5G |
| Barnyardgrass | 3C,9H | 3C,9H | 3C,8H | 2C,6H | 4C,8H | 9C | 4C,9H |
| Wild Oats | 3C,5G | — | 4C,8G | 0 | 3G | 3C,9G | 0 |
| Wheat | 3G | 2C,8G | 2C,7G | 0 | 3G | 8G | 0 |
| Corn | 2C,9H | 2C,9G | 3C,9H | 0 | 3C,9H | 9C | 3C,8H |
| Soybean | 2C,2H | 2C,7H | 3C,6H | 2C,4H | 4H | 5C,9G | 3C,9G,7X |
| Rice | 4C,9G | 5C,9G | 4C,9H | 4C,9G | 4C,9G | 9C | 6C,9G |
| Sorghum | 2C,8H | 9G | 4C,9G | 4C,9H | 4C,9G | 9C | 6C,9H |
| Sugar beet | 9C | 0 | 9C | 10C | 9C | 9C | 5C,9G |
| Cotton | 2C,8G | 5C,9G | 2C,8G | 4C,9G | 5G | 9C | 9C |
| Velvetleaf | — | 2C,9G | 3C,9G | 2C,5G | 4C,9G | 9C | 10C |
| Cheatgrass | — | 2C,5G | 2C,5G | 0 | 5G | 9C | 6C,9G |
| PRE-EMERGENCE | | | | | | | |
| Morningglory | 3G | 3G | 7G | 2C,2H | 4G | 10C | 10C |
| Cocklebur | 4G | — | 9H | 3C,8H | 8G | 9H | — |
| Sicklepod | 0 | — | — | — | — | — | — |
| Nutsedge | 0 | 6G | 6G | 0 | 5G | 10E | 10E |
| Crabgrass | 0 | 0 | 5G | 0 | 0 | 2C,5G | 4C,7G |
| Barnyardgrass | 1H | 3C,9H | 4C,9H | 3C,8H | 2C,5H | 5C,9H | 5C,8H |
| Wild Oats | 5G | 6G | 2C,8G | 3C,8G | 6G | 4C,9G | 4C,8G |
| Wheat | 5G | 6G | 9G | 2C,7G | 4G | 3C,9H | 7G |
| Corn | 9G | 2C,7G | 2C,8G | 3C,7G | 2C,6G | 3C,8H | 3C,8G |
| Soybean | 5G | 0 | 2C,5G | 2C | 2C | 3C,8H | 2C,6H |

TABLE A-continued

| | | | | | | | |
|---|---|---|---|---|---|---|---|
| Rice | 5G | 5C,9G | 9H | 3C,8G | 5C,9H | 10E | 3C,9H |
| Sorghum | 2C,9G | 2C,9G | 9H | 3C,7G | 2C,9H | 7C,9H | 3C,8G |
| Sugar beet | 4G | 8G | 9G | 9C | 5C,9G | 6C,9G | 9C |
| Cotton | 6G | 2G | 7G | 2C | 2C,4G | 6C,9G | 9G |
| Velvetleaf | — | 8G | 9G | 8G | 9G | 9C | 5C,9G |
| Cheatgrass | — | 7G | 8G | 2C,8G | 3C,8G | 10E | 4C,9H |

What is claimed is:
1. A compound of the formula

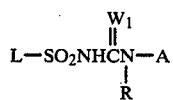

and agriculturally suitable salts thereof wherein
$W_1$ is O or S;
R is H or $CH_3$;
L is

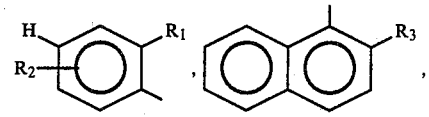

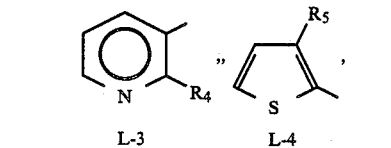

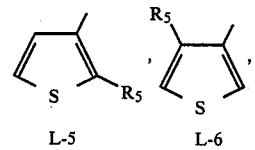

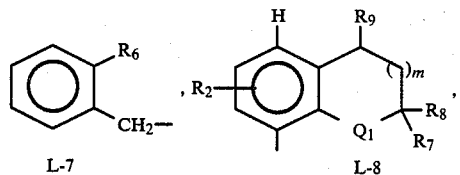

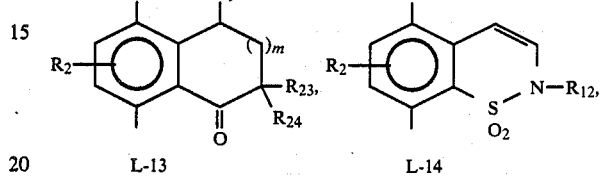

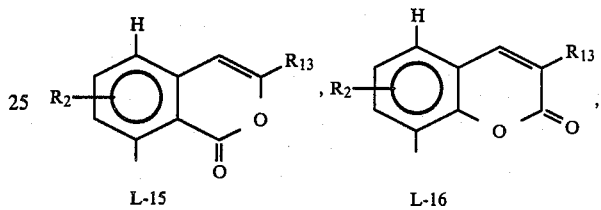

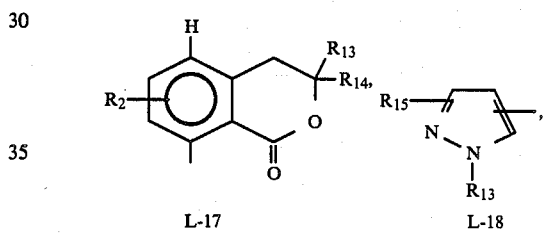

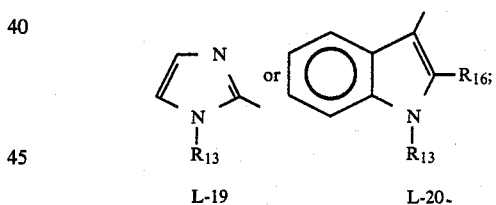

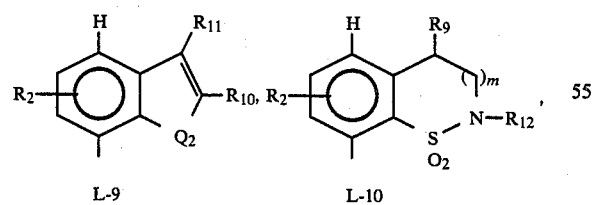

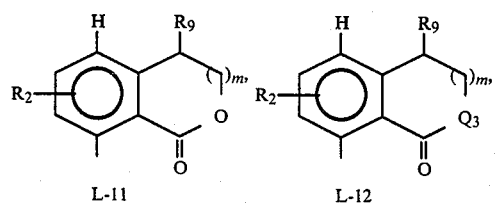

$R_1$ is $OCH_2CH_2OCH_3$, $CO_2R_{17}$, $SO_2NR_{18}R_{19}$, $SO_2N(OCH_3)CH_3$, $OSO_2R_{20}$, $WCF_3$, $WCHF_2$, $C_3-C_4$ alkenyloxy, $C_3-C_4$ alkynyloxy, $C_1-C_2$ alkyl substituted with $OCH_3$ or $OCH_2CH_3$, $C_6H_5$, $C_3-C_4$ alkynyl, $CH=CHCF_3$, $CH=CHBr$, or Q;
Q is

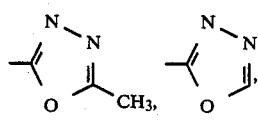

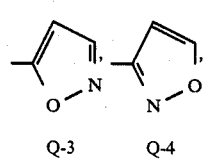

-continued

Q-5, Q-6, Q-7, Q-8, Q-9, Q-10, Q-11, Q-12, Q-13, Q-14, Q-15, Q-16, Q-17, Q-18, Q-19, Q-20

$R_2$ is H, F, Cl, Br, $CF_3$, $C_1$-$C_2$ alkyl, $C_1$-$C_2$ alkoxy, $C_1$-$C_2$ alkylthio, $C_2$-$C_3$ alkoxyalkyl, $C_2$-$C_3$ alkylthioalkyl or $OCF_2H$;

$R_3$ is H, $CH_3$, $OCH_3$, F, Cl, Br, $SO_2N(CH_3)_2$, $OSO_2CH_3$ or $S(O)_nCH_3$;

$R_4$ is $CH_3$, $CH_2CH_3$, $OCH_3$, $OCH_2CH_3$, F, Cl, Br, $SO_2NR_{18}R_{19}$, $SO_2N(OCH_3)CH_3$, $S(O)_nR_{21}$, $C_3$-$C_4$ alkenyloxy, $CH_2OCH_3$ or $CH_2OCH_2CH_3$;

$R_5$ is $C_1$-$C_3$ alkyl, F, Cl, Br, $NO_2$, $CO_2R_{17}$, $SO_2NR_{18}R_{19}$, $SO_2N(OCH_3)CH_3$ or $S(O)_nR_{21}$;

$R_6$ is Cl, $NO_2$, $CO_2CH_3$, $CO_2CH_2CH_3$, $SO_2N(CH_3)_2$, $OSO_2CH_3$, $SO_2CH_3$, $SO_2CH_2CH_3$, $OCH_3$ or $OCH_2CH_3$;

$R_7$ is H, $CH_3$ or $CH_2CH_3$;
$R_8$ is H, $CH_3$ or $CH_2CH_3$;
$R_9$ is H or $CH_3$;
$R_{10}$ is H or $CH_3$;
$R_{11}$ is H or $CH_3$;
$R_{12}$ is H, $C_1$-$C_5$ alkyl, $C_2$-$C_3$ alkoxycarbonyl, $C_2$-$C_3$ alkylcarbonyl, $C_1$-$C_3$ alkyl substituted by 1-3 halogens selected from 0-3 F, 0-3 Cl or 0-1 Br, $C_2$-$C_4$ alkyl substituted by $OCH_3$, $C_3$-$C_4$ alkenyl, $C_3$-$C_4$ alkynyl or benzyl;
$R_{13}$ is H or $C_1$-$C_3$ alkyl;
$R_{14}$ is H or $CH_3$;
$R_{15}$ is $C_1$-$C_3$ alkyl, F, Cl, Br, $NO_2$, $CO_2R_{17}$, $SO_2NR_{18}R_{19}$, $SO_2R_{21}$ or $OCF_2H$;
$R_{16}$ is H, $CO_2CH_3$, $CO_2CH_2CH_3$, $SO_2CH_3$ or $SO_2CH_2CH_3$;
$R_{17}$ is $C_1$-$C_4$ alkyl, $CH_2CH_2OCH_3$, $CH_2CH_2Cl$ or $CH_2CH=CH_2$;
$R_{18}$ is H or $C_1$-$C_3$ alkyl;
$R_{19}$ is $C_1$-$C_3$ alkyl;
$R_{20}$ is $C_1$-$C_3$ alkyl or $N(CH_3)_2$;
$R_{21}$ is $C_1$-$C_3$ alkyl or $CH_2CH=CH_2$;
$R_{22}$ is H or $C_1$-$C_3$ alkyl;
$R_{23}$ is H or Cl;
$R_{24}$ is H or Cl;
$R_{25}$ is H or $CH_3$;
m is 0 or 1;
n is 0 to 2;
$Q_1$ is O, S, $SO_2$ or $NR_{14}$;
$Q_2$ is O or S;
$Q_3$ is S or $NR_{22}$;
W is O, S or $SO_2$;
A is

A-1

X is H, $C_1$-$C_3$ alkyl, $C_1$-$C_3$ alkoxy, $C_1$-$C_3$ haloalkyl, $C_1$-$C_3$ haloalkoxy, $C_2$-$C_4$ alkoxyalkoxy, $C_1$-$C_3$ alkylamino, di($C_1$-$C_2$ alkyl)amino, amino or cyclopropyl;
Y is H, $C_1$-$C_5$ alkyl, Br, I, phenyl optionally substituted with $CH_3$, $OCH_3$, halogen, $NO_2$, $CF_3$ or $SCH_3$, or $C_1$-$C_3$ alkyl substituted with OH, $OCH_3$, $OC_2H_5$ or F; and
Z is N;
provided that
(i) the total number of carbon atoms of $R_{18}$ and $R_{19}$ is less than or equal to four;
(ii) when m is 1, then $R_9$ is H;
(iii) when L is L-17, then $R_{13}$ and $R_{14}$ are not simultaneously H;
(iv) when L is L-18, then $R_{15}$ is adjacent to the sulfonylurea bridge $SO_2NHC(W_1)N(R)A$;
(v) when L is L-8 and $Q_1$ is $NR_{14}$, then m is 1;
(vi) when the total number of carbon atoms of X and Y is greater than four, then the combined number of carbons of the substituents on L is less than or equal to four; and
(vii) when L is L-8, L-9, L-11, L-12 or L-17 and $R_2$ is $C_2$-$C_3$ alkoxyalkyl or $C_2$-$C_3$ alkylthioalkyl, then Y is other than H or $C_1$-$C_2$ alkyl.

2. Compounds of claim 1 where R is H and $W_1$ is O.

3. Compounds of claim 2 where Y is H or $C_1$–$C_3$ alkyl.

4. Compounds of claim 3 where L is L-1, L-2, L-3, L-4, L-5, L-6, L-8, L-9, L-10, L-11, L-12, L-13, L-17 or L-18, $Q_1$ is O, S or $SO_2$ and X is $CH_3$, $CH_2CH_3$, $OCH_3$, $OCH_2CH_3$, $CH_2OCH_3$, $CH_2OCH_2CH_3$, $OCH_2CF_3$, $OCH_2CF_2H$, $OCH_2CH_2F$ or $OCF_2H$.

5. Compounds of claim 4 where $R_1$ is $CO_2R_{17}$, $SO_2NR_{18}R_{19}$, $SO_2N(OCH_3)CH_3$, $WCF_3$, $WCHF_2$,

[chemical structures]

$R_2$ is H, F, Cl, $CH_3$, $OCH_3$ or $SCH_3$;
$R_3$ is $CH_3$, $OCH_3$, Cl, Br, $OSO_2CH_3$ or $S(O)_nCH_3$;
$R_4$ is $CH_3$, $OCH_3$, Cl, $SO_2N(CH_3)_2$, $SO_2CH_3$ or $SO_2CH_2CH_3$;
$R_5$ is $CH_3$, Cl, $NO_2$, $CO_2R_{17}$, $SO_2N(CH_3)_2$, $SO_2CH_3$ or $SO_2CH_2CH_3$;
$R_7$ is H or $CH_3$;
$R_8$ is H or $CH_3$;
$R_9$ is H;
$R_{11}$ is H;
$R_{12}$ is H, $C_1$–$C_4$ alkyl, $CH_2CH_2OCH_3$ or $CH_2CH\!=\!CH_2$;
$R_{13}$ is H or $CH_3$;
$R_{15}$ is $CH_3$, $CH_2CH_3$, Cl, $NO_2$, $CO_2CH_3$, $CO_2CH_2CH_3$, Br, $SO_2N(CH_3)_2$, $SO_2CH_3$, $SO_2CH_2CH_3$ or $OCF_2H$;
$R_{18}$ is H or $CH_3$;
$R_{19}$ is $C_1$–$C_2$ alkyl; and
W is O or S.

6. Compounds of claim 5 where X is $CH_3$, $CH_2CH_3$, $OCH_3$ or $OCH_2CH_3$ and Y is H or $CH_3$.

7. Compounds of claim 6 where L is L-1 and $R_1$ is $CO_2CH_3$, $CO_2CH_2CH_3$, $SO_2N(CH_3)_2$, or $OCF_2H$.

8. Compounds of claim 6 where L is L-2.
9. Compounds of claim 6 where L is L-4.
10. Compounds of claim 6 where L is L-5.
11. Compounds of claim 6 where L is L-8.
12. Compounds of claim 6 where L is L-9.
13. Compounds of claim 6 where L is L-10.
14. Compounds of claim 6 where L is L-11.
15. Compounds of claim 6 where L is L-12.
16. Compounds of claim 6 where L is L-13.
17. Compounds of claim 6 where L is L-17.
18. Compounds of claim 6 where L is L-18.
19. A compound according to claim 1, wherein when L is L-4, then $R_5$ is other than $C_1$ to $C_3$ alkyl.

20. The compound of claim 1 that is 2-[[(4-ethynyl-6-methoxy-1,3,5-triazin-2-yl)aminocarbonyl]aminosulfonyl]benzoic acid, methyl ester.

21. The compound of claim 1 that is N'-[(4-ethynyl-6-methoxy-1,3,5-triazin-2-yl)aminocarbonyl]N,N-dimethyl-1,2-benzenedisulfonamide.

22. A composition for the control of undesirable vegetation consisting essentially of a compound of claim 1 and at least one of (a) a surface active agent, and (b) a solid or liquid diluent.

23. A composition for the control of undesirable vegetation consisting essentially of a compound of claim 2 and at least one of (a) a surface active agent, and (b) a solid or liquid diluent.

24. A composition for the control of undesirable vegetation consisting essentially of a compound of claim 3 and at least one of (a) a surface active agent, and (b) a solid or liquid diluent.

25. A composition for the control of undesirable vegetation consisting essentially of a compound of claim 4 and at least one of (a) a surface active agent, and (b) a solid or liquid diluent.

26. A composition for the control of undesirable vegetation consisting essentially of a compound of claim 5 and at least one of (a) a surface active agent, and (b) a solid or liquid diluent.

27. A composition for the control of undesirable vegetation consisting essentially of a compound of claim 6 and at least one of (a) a surface active agent, and (b) a solid or liquid diluent.

28. A composition for the control of undesirable vegetation consisting essentially of a compound of claim 7 and at least one of (a) a surface active agent, and (b) a solid or liquid diluent.

29. A composition for the control of undesirable vegetation consisting essentially of a compound of claim 8 and at least one of (a) a surface active agent, and (b) a solid or liquid diluent.

30. A composition for the control of undesirable vegetation consisting essentially of a compound of claim 9 and at least one of (a) a surface active agent, and (b) a solid or liquid diluent.

31. A method for the control of undesirable vegetation comprising applying to the locus of such vegetation an herbicidally effective amount of a compound of claim 1.

32. A method for the control of undesirable vegetation comprising applying to the locus of such vegetation an herbicidally effective amount of a compound of claim 2.

33. A method for the control of undesirable vegetation comprising applying to the locus of such vegetation an herbicidally effective amount of a compound of claim 3.

34. A method for the control of undesirable vegetation comprising applying to the locus of such vegetation an herbicidally effective amount of a compound of claim 4.

35. A method for the control of undesirable vegetation comprising applying to the locus of such vegetation an herbicidally effective amount of a compound of claim 5.

36. A method for the control of undesirable vegetation comprising applying to the locus of such vegetation an herbicidally effective amount of a compound of claim 6.

37. A method for the control of undesirable vegetation comprising applying to the locus of such vegetation an herbicidally effective amount of a compound of claim 7.

38. A method for the control of undesirable vegetation comprising applying to the locus of such vegetation an herbicidally effective amount of a compound of claim 8.

39. A method for the control of undesirable vegetation comprising applying to the locus of such vegetation an herbicidally effective amount of a compound of claim 9.

* * * * *